United States Patent
Peris et al.

(10) Patent No.: US 11,134,761 B2
(45) Date of Patent: Oct. 5, 2021

(54) WATER DISPERSING BAG

(71) Applicant: Fisher & Paykel Healthcare Limited, Auckland (NZ)

(72) Inventors: Robbie Gavin Peris, Auckland (NZ); Andrew Paul Maxwell Salmon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 10 days.

(21) Appl. No.: 16/302,458

(22) PCT Filed: May 12, 2017

(86) PCT No.: PCT/IB2017/052786
§ 371 (c)(1),
(2) Date: Nov. 16, 2018

(87) PCT Pub. No.: WO2017/199143
PCT Pub. Date: Nov. 23, 2017

(65) Prior Publication Data
US 2019/0200715 A1     Jul. 4, 2019

Related U.S. Application Data

(60) Provisional application No. 62/339,013, filed on May 19, 2016.

(51) Int. Cl.
*A45C 3/00* (2006.01)
*A61B 50/30* (2016.01)
(Continued)

(52) U.S. Cl.
CPC ............... *A45C 3/001* (2013.01); *A45C 3/00* (2013.01); *A45C 13/008* (2013.01); *A45C 13/02* (2013.01);
(Continued)

(58) Field of Classification Search
CPC ......... A45C 3/001; A45C 3/00; A45C 13/008; A45C 13/02; A45C 2013/206;
(Continued)

(56) References Cited

U.S. PATENT DOCUMENTS 5,323,897 A * 6/1994 Sperber ................. D06F 95/002
206/287
5,660,868 A * 8/1997 Yeager ................. B65D 81/264
206/204
(Continued)

FOREIGN PATENT DOCUMENTS

CN          101415469 A       4/2009
WO        WO-9205089 A1 *    4/1992    ........... B65D 81/264
WO       WO 2015/070289      5/2015

OTHER PUBLICATIONS

Jul. 26, 2017 International Search Report for International Application No. PCT/IB2017/052786 filed on May 12, 2017.
(Continued)

*Primary Examiner* — Jes F Pascua
(74) *Attorney, Agent, or Firm* — Knobbe, Martens, Olson & Bear, LLP

(57) ABSTRACT

A water dispersing bag for transporting, storing, and/or holding medical equipment is provided. In some configurations, the bag can include a lower portion, an upper portion, a handle, and a shoulder strap. The handle can include a handle strap. The shoulder strap can include a shoulder strap connector. In some embodiments, the bag can include a locking mechanism that can allow access to an interior of the bag.

9 Claims, 21 Drawing Sheets

(51) Int. Cl.
*A45C 13/00* (2006.01)
*A61B 50/31* (2016.01)
*A61M 16/00* (2006.01)
*A45C 13/02* (2006.01)
*A61B 50/00* (2016.01)

(52) U.S. Cl.
CPC .............. *A61B 50/30* (2016.02); *A61B 50/31* (2016.02); *A61M 16/0003* (2014.02); *A45C 2003/002* (2013.01); *A45C 2013/026* (2013.01); *A61B 2050/0088* (2016.02); *A61B 2050/301* (2016.02); *A61B 2050/3008* (2016.02); *A61B 2050/3011* (2016.02); *A61M 2209/06* (2013.01)

(58) Field of Classification Search
CPC ..... A45C 2209/06; A61B 50/30; A61B 50/31; A61B 2050/0088; A61B 2050/3008; A61B 2050/301; A61B 2050/3011; A61M 2209/06
USPC .......................................... 383/100–103, 117
See application file for complete search history.

(56) References Cited

U.S. PATENT DOCUMENTS

| | | | | |
|---|---|---|---|---|
| 5,839,572 A | * | 11/1998 | Yeager | B65D 31/12 206/204 |
| 5,845,769 A | * | 12/1998 | Yeager | B65D 31/12 206/204 |
| 6,632,403 B1 | * | 10/2003 | Barmore | B65D 33/34 206/223 |
| 6,652,145 B2 | * | 11/2003 | Valdez | A45C 3/08 190/108 |
| 7,798,323 B1 | | 9/2010 | McCann et al. | |
| 8,777,001 B1 | | 7/2014 | Bennett | |
| D840,675 S | * | 2/2019 | Peris | D3/203.1 |
| 2006/0043135 A1 | * | 3/2006 | Lindsey | A45F 3/04 224/576 |
| 2007/0084866 A1 | * | 4/2007 | Saeugling | B65F 1/0006 220/495.06 |
| 2007/0095680 A1 | * | 5/2007 | Spektor | A61M 16/0078 206/210 |
| 2007/0251846 A1 | * | 11/2007 | Brim, III | A45C 13/02 206/320 |
| 2010/0187135 A1 | * | 7/2010 | Broering | B65F 1/0006 206/204 |
| 2011/0301399 A1 | * | 12/2011 | Perlman | C02F 11/008 588/2 |
| 2011/0311166 A1 | * | 12/2011 | Pascua | A45C 3/001 383/41 |
| 2012/0152996 A1 | * | 6/2012 | McDonald | A45C 7/0059 224/602 |
| 2013/0322786 A1 | * | 12/2013 | Nassanian | A45C 3/001 383/25 |
| 2016/0101916 A1 | * | 4/2016 | Grijalva Varillas | B32B 5/142 383/102 |
| 2016/0193437 A1 | * | 7/2016 | Bao | A61M 16/024 128/203.14 |
| 2017/0258189 A1 | * | 9/2017 | Goldfinger | B62B 3/1464 |
| 2018/0078049 A1 | * | 3/2018 | Rhen | A45C 3/00 |

OTHER PUBLICATIONS

Chinese Office Action for Application No. 201780030322.2 dated Oct. 10, 2020, 11 pages.

* cited by examiner

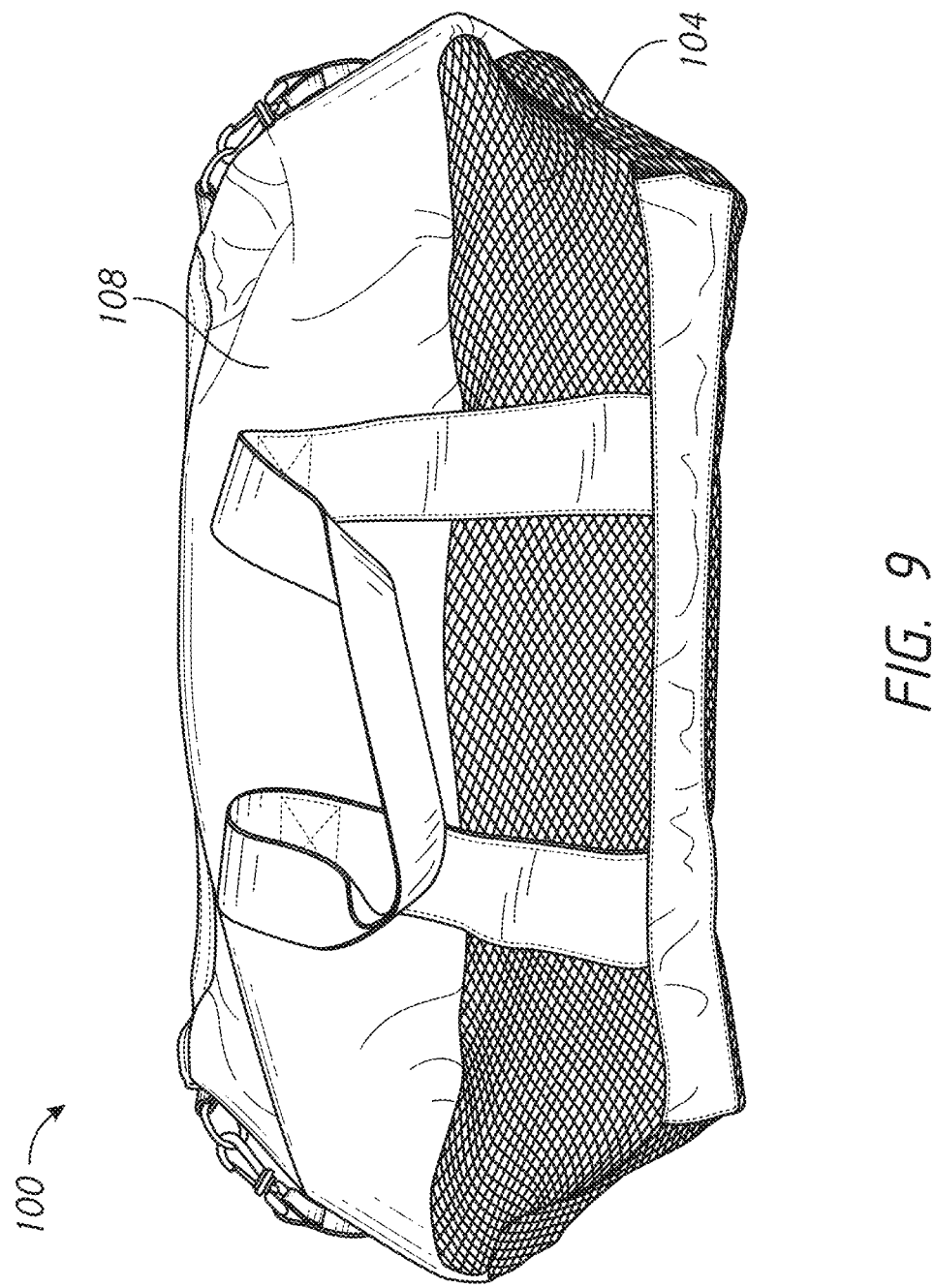

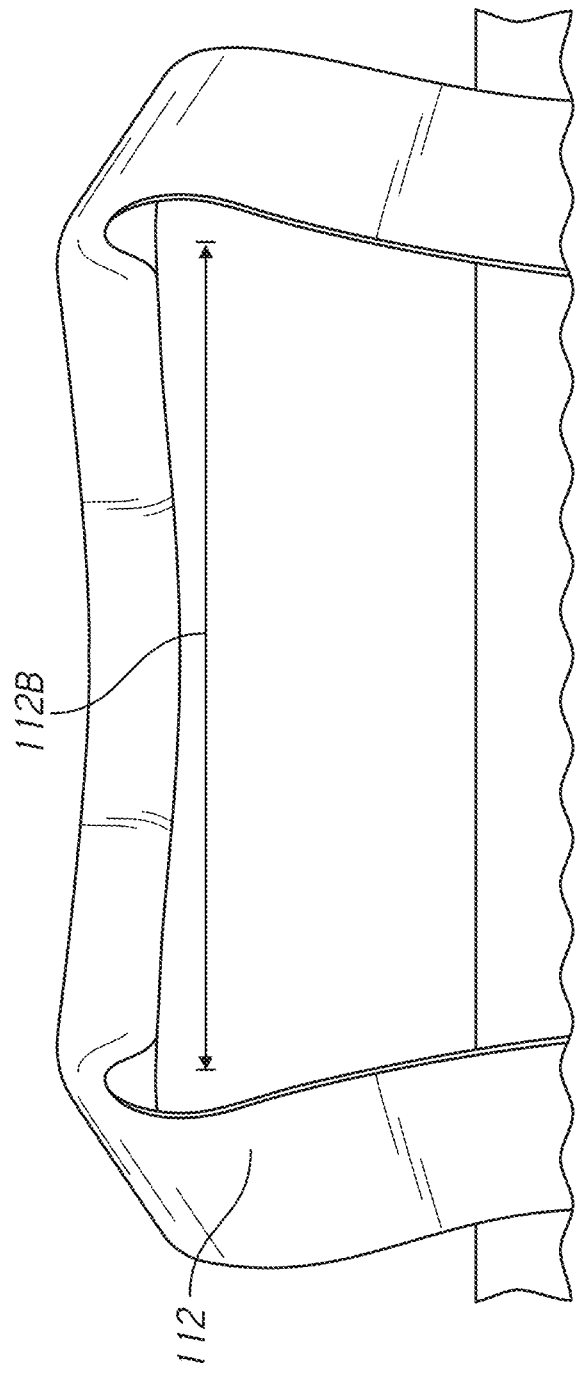

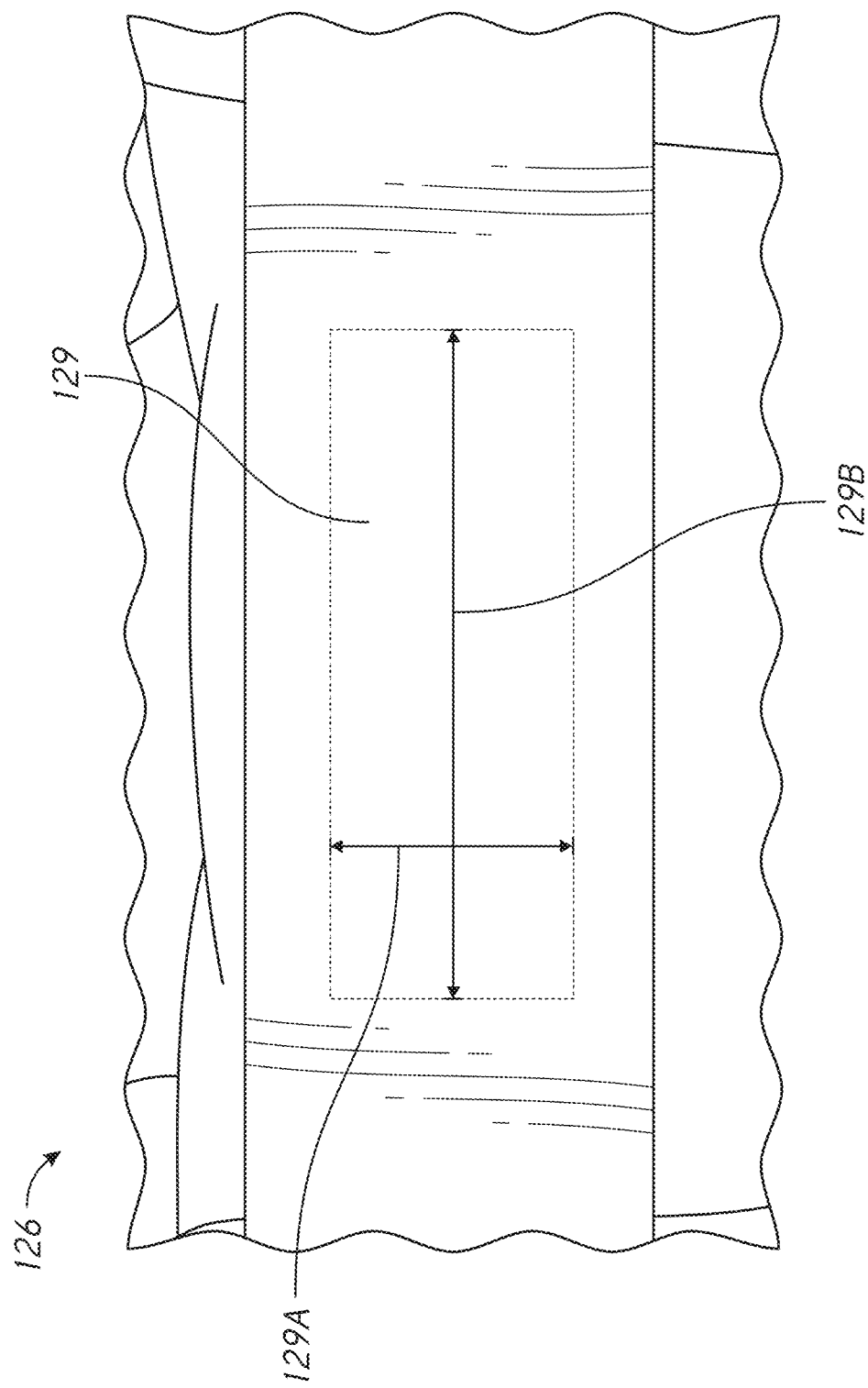

WATER DISPERSING BAG

INCORPORATION BY REFERENCE

This application is a U.S. National Phase application of PCT Application No. PCT/IB2017/052,786, filed May 12, 2017, which claims priority to U.S. Provisional Application No. 62/339,013, filed 19 May 2016, the entirety of each of which is hereby incorporated by reference herein and made a part of the present disclosure.

FIELD OF THE DISCLOSURE

The present disclosure generally relates to multipurpose bags. In particular, the present disclosure relates to a water dispersing bag that can be used for storing, transporting, and/or holding medical equipment, such as CPAP machines.

BACKGROUND

Medical equipment is generally very specialized and often very costly. Special care should be taken when carrying, transporting, and/or storing medical equipment to prevent damage. One type of specialized medical equipment that is often transported is a CPAP machine. CPAP machines often have a water reservoir used to humidify pressurized air provided to an airway of a patient. If the water reservoir is not properly emptied and the machine dried before transport, the water may leak out causing damage to the machine and surrounding materials or area. Traditional bags may not be suitable for protecting the medical equipment and its electronic components from water damage.

SUMMARY

Accordingly, it is an object of certain embodiments of the present disclosure to provide an improved bag that can be used for storing, transporting and/or holding medical equipment that overcomes the shortcomings of traditional bags, or which at least provides the public with a useful choice. The systems, methods and devices described herein have innovative aspects, no single one of which is indispensable or solely responsible for their desirable attributes. Without limiting the scope of the claims, some of the advantageous features will now be summarized.

The present disclosure provides a medical device carrying bag that provides for relatively small and portable bag that is effective at disposing of liquid spilled in the bag. The bag can allow the water to be dispersed throughout the bag quickly and/or allow the water to drain from the bag more effectively.

According to some embodiments, a water dispersing bag can comprise a bottom surface, a first side wall including a lower portion with an insert and utilizing a first material; and an upper portion utilizing a second material; wherein the lower portion is more permeable than the upper portion.

In some embodiments, the bottom surface is less permeable than the lower portion. In some embodiments, the lower portion extends at least partially around the bag. In some embodiments, the lower portion comprises an open cell foam material disposed between a first layer of a mesh fabric and a second layer of a mesh fabric. In some embodiments, the upper portion comprises a polyester canvas material.

In some embodiments, the bottom surface comprises a polyester canvas material. In some embodiments, the water dispersing bag further comprises a first handle strap spanning at least a first length of the first side wall, and a second handle strap spanning at least a second length of the second side wall. In some embodiments, the water dispersing bag further comprises an opening mechanism, the opening mechanism configured to allow access to an interior.

In some embodiments, a ratio between a vertical dimension of the lower portion to a vertical dimension of the first side wall is approximately 1:2.57. In some embodiments, a vertical dimension of the lower portion is approximately 70 mm, and wherein a vertical dimension of the first side wall section is approximately 180 mm.

According to some embodiments, a water dispersing bag comprises a bottom surface; at least one side wall; an opening mechanism configured to allow access to an interior portion, the interior portion including a first divider extending from a first side wall and a second side wall of the at least one side wall, wherein the first divider comprises a fixed connection to a first interior surface of the first side wall and a detachable connection to a second interior surface of the second side wall.

In some embodiments, the at least one side wall comprises a lower portion and an upper portion. In some embodiments, the first divider is pivotable about the fixed connection between a first position and a second position at least partially adjacent to the first interior surface. In some embodiments, the interior portion comprises a second divider spanning a length of the interior portion, and wherein the second interior divider comprises a fixed connection to the second interior surface, and a removable connection to the first interior surface.

In some embodiments, the second divider is pivotable about the fixed connection between a first position and a second position at least partially adjacent to the second interior surface. In some embodiments, the first divider is substantially parallel to the second divider. In some embodiments, the first divider and second divider are displaced in a direction perpendicular to the bottom surface.

In some embodiments, the first divider is configured to be disconnected and pivoted about the fixed connection of the first divider, and the second divider is configured to be disconnected and pivoted about the fixed connection of the second divider to form an undivided interior portion. In some embodiments, the first divider is configured to attach to a first adjacent side wall and the second divider is configured to attach to a second adjacent side wall.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 9 shows an embodiment of the water dispersing bag.

FIGS. 14A and 14B shows a front view of an embodiment of the water dispersing bag including a handle.

FIGS. 18A and 18B show an embodiment of a luggage strap of the water dispersing bag.

DETAILED DESCRIPTION

Figure 1:
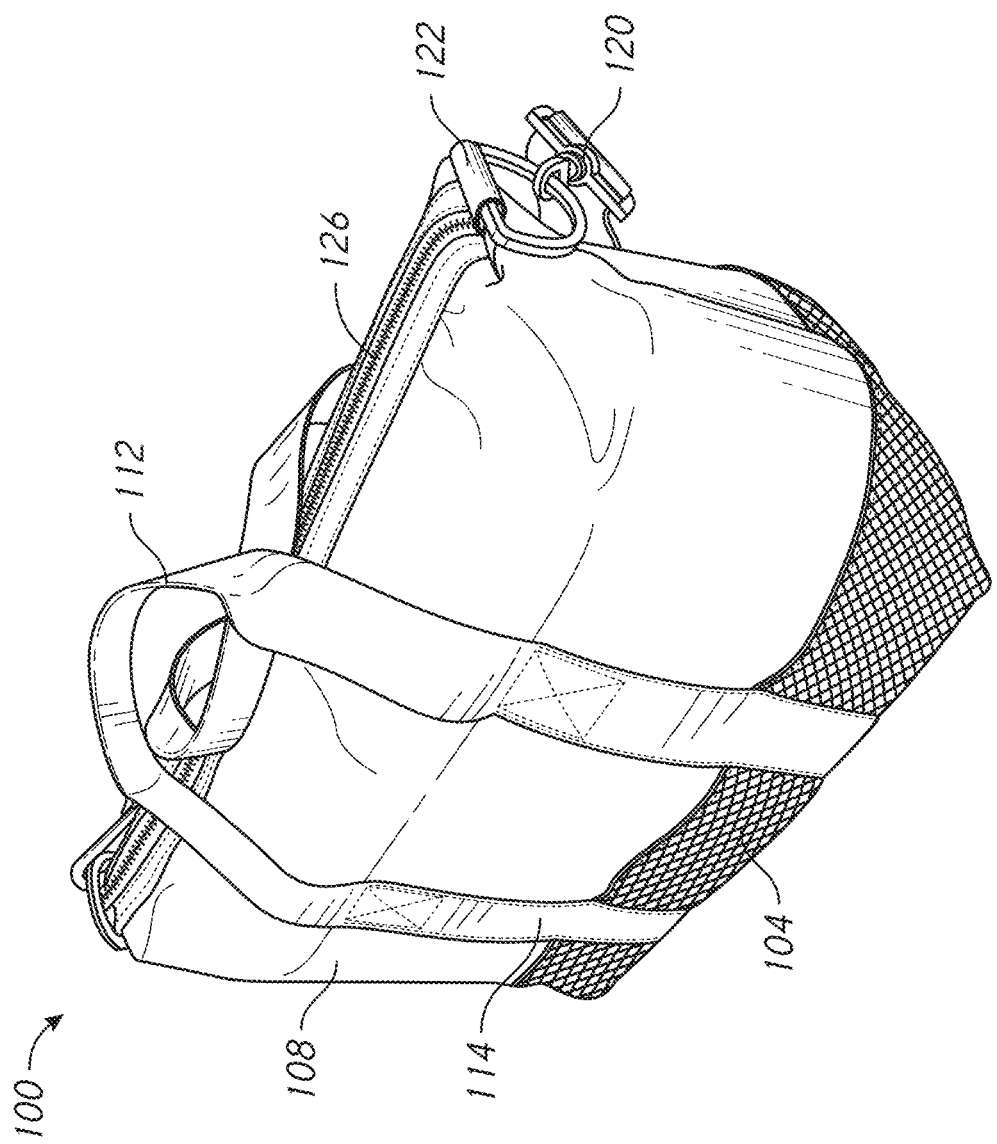
FIG. 1 shows an outer perspective view of an embodiment of a water dispersing bag.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

This disclosure provides a water dispersing bag that can store, transport, carry, and/or otherwise hold medical equipment, such as CPAP machines. Some CPAP machines can store liquid in a humidifier, for example. The bag can facilitate the quick dispersal of spilled liquids, directing the liquids away from the medical equipment. The bag can direct the liquids outside of the bag. In many medical equipment systems, there are a number of electrical components (for example, a USB port and/or battery) which water or other liquids can potentially enter and disrupt.

Traditional methods of transporting and/or carrying medical equipment that contains water, for example, can spill the liquid easily. The liquid can sit in the carrying device, seep into the medical equipment, and potentially harm the equipment. Thus, traditional methods and devices may ineffectively protect medical equipment from damage. Many traditional methods and devices similarly do not adequately dispose of liquids that are spilled within the device.

In contrast, embodiments of the bag disclosed herein can mitigate the effect of accidental spills of liquid, for example from a user and/or the medical equipment, such as a CPAP machine. In some embodiments, the bag can include multiple portions. Each of the portions can include various permeability rates.

Thus, the bag can protect the electronic components of the medical equipment by providing better liquid dispersion across a lower portion of the bag. The bag can allow the liquid to be drained from the bag more quickly through the lower portion.

As a result, the bag can enhance the reliability and durability of the medical equipment. The bag can increase the value of the medical equipment in some instances. The additional protection afforded to the medical equipment can allow for use of the medical equipment over a longer time period.

In some configurations, the bag can be aesthetically pleasing. The bag can be used as a multipurpose bag, not solely for carrying medical equipment. For example, the bag can be used as a gym bag or general purpose bag.

FIG. 1 illustrates a perspective view of an embodiment of the water dispersing bag 100. The bag 100 can include a lower portion 104, an upper portion 108, a handle 112, and a shoulder strap 120. The handle 112 can include a handle strap 114. The shoulder strap 120 can include a shoulder strap connector 122. In some embodiments, the bag 100 can include a locking mechanism 126. In some embodiments, the locking mechanism can include a zipper 126. Overall, the bag 100 can be substantially rectangular in shape. In some embodiments, the bag 100 can be oval-shaped, circular, and/or trapezoidal.

Lower Portion

Figure 2:
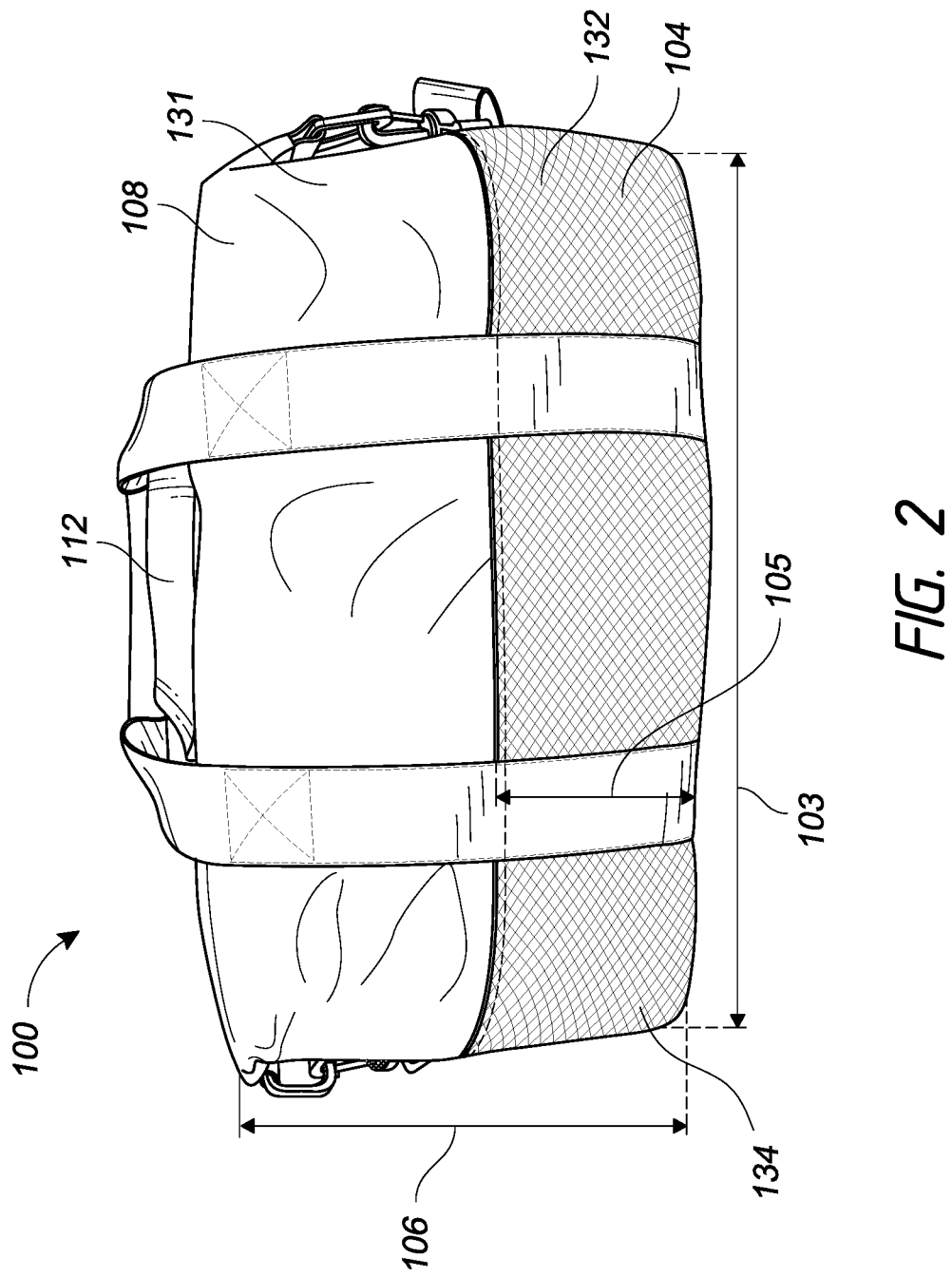
FIG. 2 shows a front view of an embodiment of a water dispersing bag.

FIG. 2 illustrates a front view of an embodiment of the bag 100. The lower portion 104 can extend partially around the bag 100. In some embodiments the lower portion 104 extends around the entire bag 100. The lower portion can include a lower interior surface 130 and a lower exterior surface 132. The lower interior surface 130 and the lower exterior surface 132 of the lower portion 104 can include a variety of materials. In some embodiments, the lower interior surface 130 and the lower exterior surface 132 can include different materials. In some embodiments, the lower interior surface 130 and the lower exterior surface 132 can include the same material. For example, the lower exterior surface 132 and lower interior surface 130 can both include a mesh material, such as black 200 gsm sandwich mesh. The mesh material can include a plurality of large openings within the mesh. In some embodiments, the mesh material can include a plurality of small openings within the mesh. In yet other embodiments, the mesh material can include a plurality of large and small openings within the mesh.

In some embodiments, the lower portion 104 can include an insert 134 disposed between the lower exterior surface 132 and the lower interior surface 130. In some configurations, the insert 134 can include a foam-like material, such as black open cell 20 ppi or less filter foam. The insert 134 can be 1 to 2, 2 to 3, 3 to 4, 4 to 5, 5 to 6, 6 to 7, 7 to 8, 8 to 9, and/or 9 to 10 or more mm thick. In some embodiments, the insert 134 can include cells and/or gas pockets within the insert 134 that can allow various amounts of liquid through the lower portion 104 and at various rates. As a result, the insert 134 can provide channels for liquid to travel through and out of the bag with minimum resistance. Similarly, the lower portion 104 can be substantially permeable and/or allow liquid to pass through quickly. In some embodiments, the lower portion is less permeable than the upper portion 108.

Advantageously, the lower portion 104 can facilitate rapid dispersion and/or draining of liquid that is disposed and/or spilled in the interior of the bag 100. As a result, the material of the lower interior surface 130 and the lower exterior surface 132 can decrease and/or minimized the amount of time liquid is exposed to any electronic instruments or components being held within the interior of the bag 100. In some embodiments, the material of the lower interior surface 130 and the lower exterior surface 132 can provide a sufficient amount of support and allow the bag 100 to maintain its structural integrity. Thus, the lower portion 104 can mitigate the effects of liquid within the interior of the bag 100.

As shown in the illustrated configuration, lower portion 104 and the upper portion 108 can be made of different materials. In some embodiments, the lower portion 104 and the upper portion 108 can be made of the same material. For example, an outer surface 131 of the upper portion 108 can include any fabric, such as polyester canvas, among others. In some embodiments an inner surface 133 of the upper portion 108 can include a lining, made of materials such as any fabric, polyester lining, and/or polyester canvas, among others. The upper portion can be less permeable than the lower portion.

In some embodiments, the lower portion 104 can include various weights and profiles. For example, the lower interior surface 130 and the lower exterior surface can both weigh 10, 25, 50, 75, 100, 125, 150, 175, 200, 225, 250, 275, and/or 300 or more gsm. In some embodiments, both the interior surface 130 and the lower exterior surface can be less than 200 gsm, for example. In other embodiments, the lower interior surface 130 and the lower exterior surface 132 can include different weights. For example, the lower interior surface 130 can weigh more than the lower exterior surface 132. In other embodiments, the lower interior surface 130 can weigh less than the lower exterior surface 132.

In some embodiments, the lower portion 104 can have various sizes. In the illustrated configuration, for example, the lower portion 104 extends vertically from a bottom surface 110 of the bag 100 at a height 105 approximately 70 mm. In some embodiments, the lower portion 104 extends vertically from the bottom surface more than 70 mm. In some embodiments, the lower portion 104 extends vertically from the bottom surface 110 less than 70 mm. For example, the lower portion 104 can extend vertically 10, 20, 30, 40, 50, 60, 80, 90, 100, 110, 120, 130, 140, and/or more millimeters from the bottom surface 110

In some embodiments, certain sizes of the lower portion 104 can maximize the ability of the bag 100 to disperse liquid without damaging the bag 100 and/or any objects, such as electrical components contained within the bag 100. The lower portion 104 can be advantageously sized to minimize costs, maximize manufacturability, and/or maintain the structural integrity of the bag 100.

In some instances, to maintain the structural integrity of the bag 100, the lower portion does not extend vertically across the entire bag 100. For example, the lower portion 104 can be sized as a ratio between the height of the lower portion 104 and the overall height 106 of the bag 100. In some instances the bag can include a height of 100, 110, 120, 130, 140, 150, 160, 170, 180, 190, 200, 210, 220, 230, 240, and/or 250 or more mm. Thus, the ratio between the height of the height of the bag 100 to the lower portion 104 can be approximately 2.57:1. In some configurations, the ratio of the height of the bag to the height of the lower portion 104 can be approximately 1.0:1.0, 1.25:1.0, 1.5:1.0, 1.75:1.0, 2.0:1.0, 2.25.0:1.0, 2.5.0:1.0, 2.75.0:1.0, 3.0:1.0, 3.25.0:1.0, 3.5:1.0, 3.75:1.0, 4.0:1.0, 4.25:1.0, 4.5:1.0, or larger.

In some embodiments, the lower portion 104 can include an overall width 103 of approximately 320 mm. In some embodiments, the width of the lower portion 104 can be approximately 100 to 200 mm, 200 to 250 mm, 250 to 300 mm, 300 to 350 mm, 350 to 400 mm, and or 400 or more millimeters wide.

Figure 3:
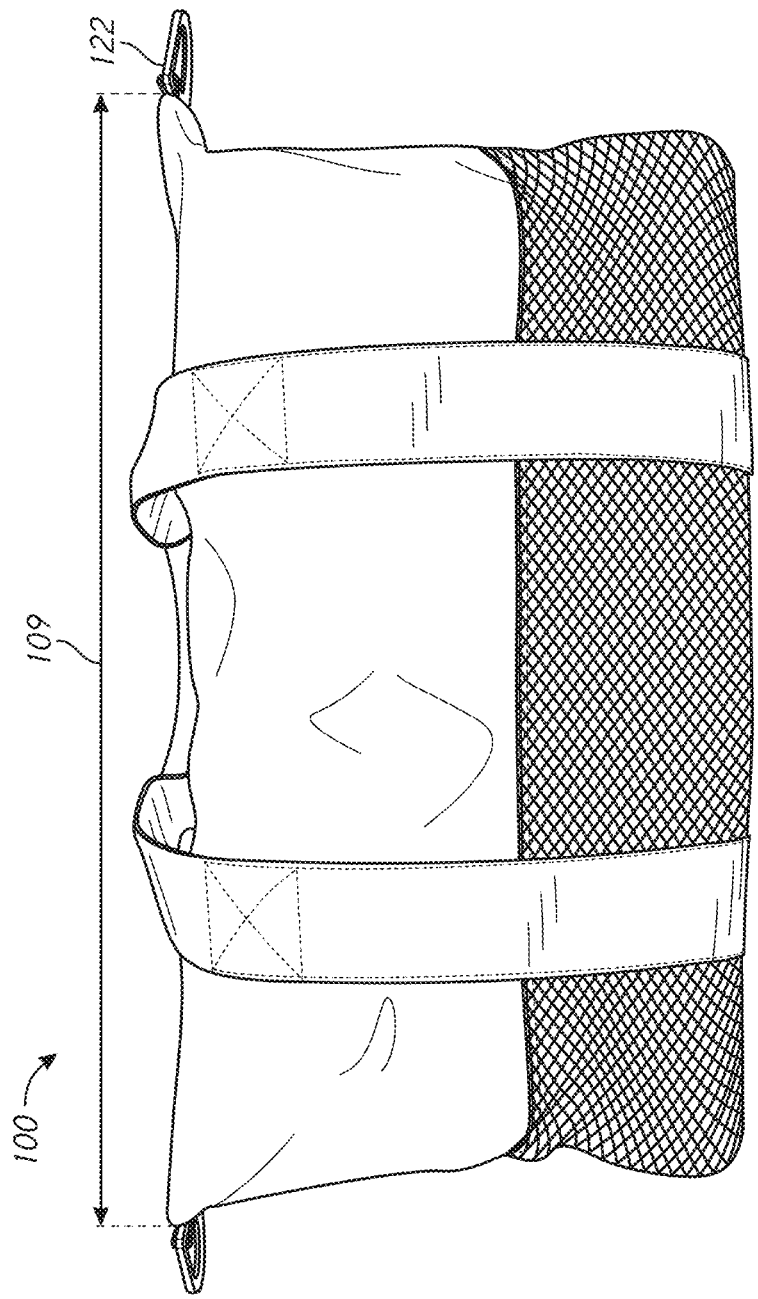
FIG. 3 shows a front view of an embodiment of the water dispersing bag.

FIG. 3 illustrates a front view of the bag 100 including the shoulder strap 120 and the shoulder strap connectors 122. In the illustrated embodiment, the shoulder strap connectors extend horizontally and are in the unfolded position. In such a configuration, a width 109 of the upper portion 108 can be 400 mm. In some embodiments, the width of the upper portion 108 is 100 to 200 mm, 200 to 300 mm, 300 to 350 mm, 350 to 400 mm, 400 to 450, 450 to 500 and or 500 or more millimeters wide.

Figure 4:
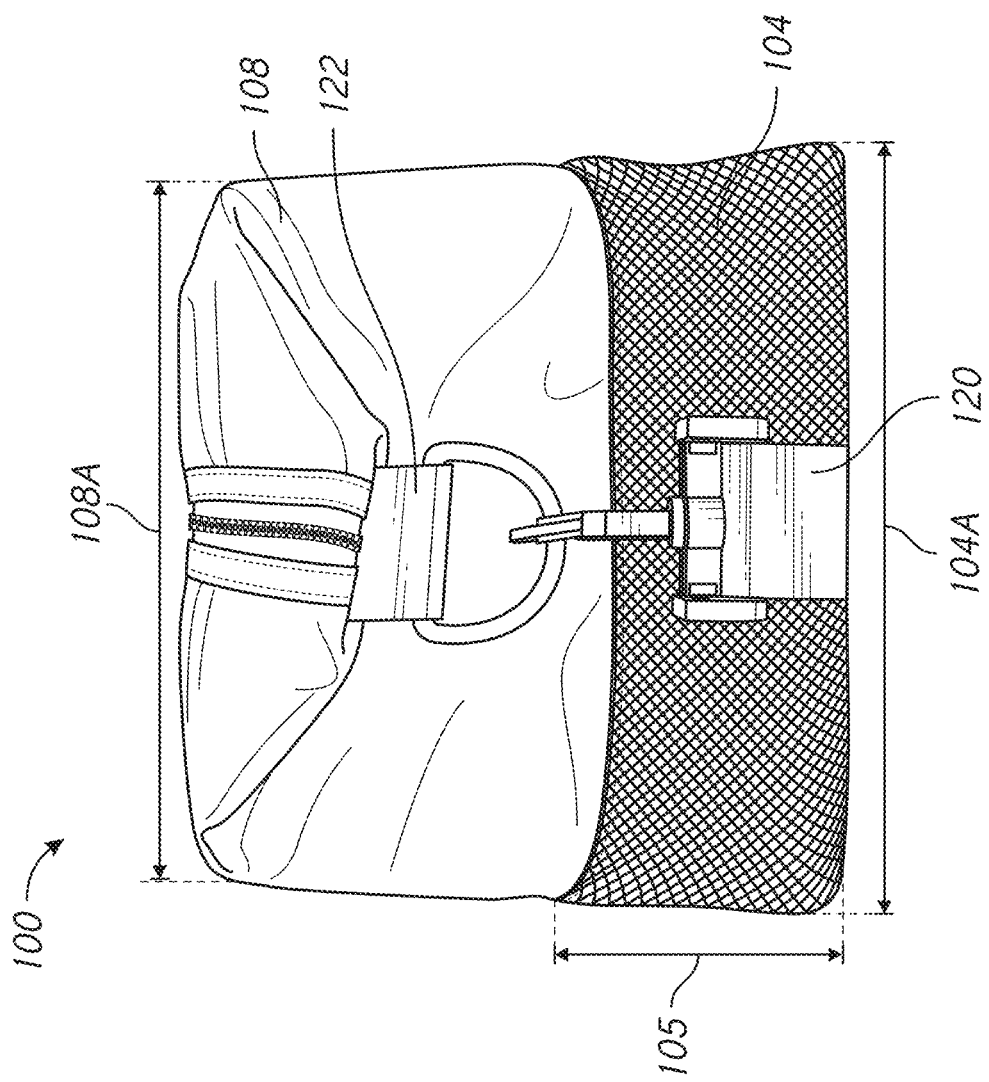
FIG. 4 shows an outer side view of an embodiment of the water dispersing bag.

As illustrated in FIG. 4, in some embodiments of the bag 100, the shoulder strap connectors 122 can be folded down. FIG. 4 illustrates a side view of the bag 100. The front profile of the bag 100 can be substantially trapezoidal, square, rectangular, oval-shaped, and/or circular, among other shapes. For example, the upper portion 108 can have an upper depth 108A and the lower portion 104 can have a lower depth 104A. The upper depth 108A can be the same, longer than, and/or shorter than the lower depth 104A. For example, in the illustrated configuration, the upper depth is smaller than the lower depth. The upper portion can have an upper depth of 190 mm and the lower portion can have a lower depth of 220 mm. In some embodiments, the upper depth 108A is approximately 150 to 160 mm, 160 to 170 mm, 180 to 190 mm, 190 mm to 200 mm, 200 to 210 and/or 210 or more millimeters deep. In some embodiments, the lower depth is approximately 190 mm to 200 mm, 200 to 210 mm, 210 to 220 mm, 220 to 230 mm, 230 to 240 mm, and/or 240 or more millimeters deep.

In some embodiments, a ratio can be determined between the lower depth and the upper depth. For example, the ratio of the lower depth to the upper depth can be 1.16:1.0. In some embodiments, the ratio of the lower depth to the upper depth is larger than 1.16 to 1.0. In some embodiments, the ratio of the lower depth to the upper depth is smaller than 1.16 to 1.0.

Interior of the Bag

Figure 5:
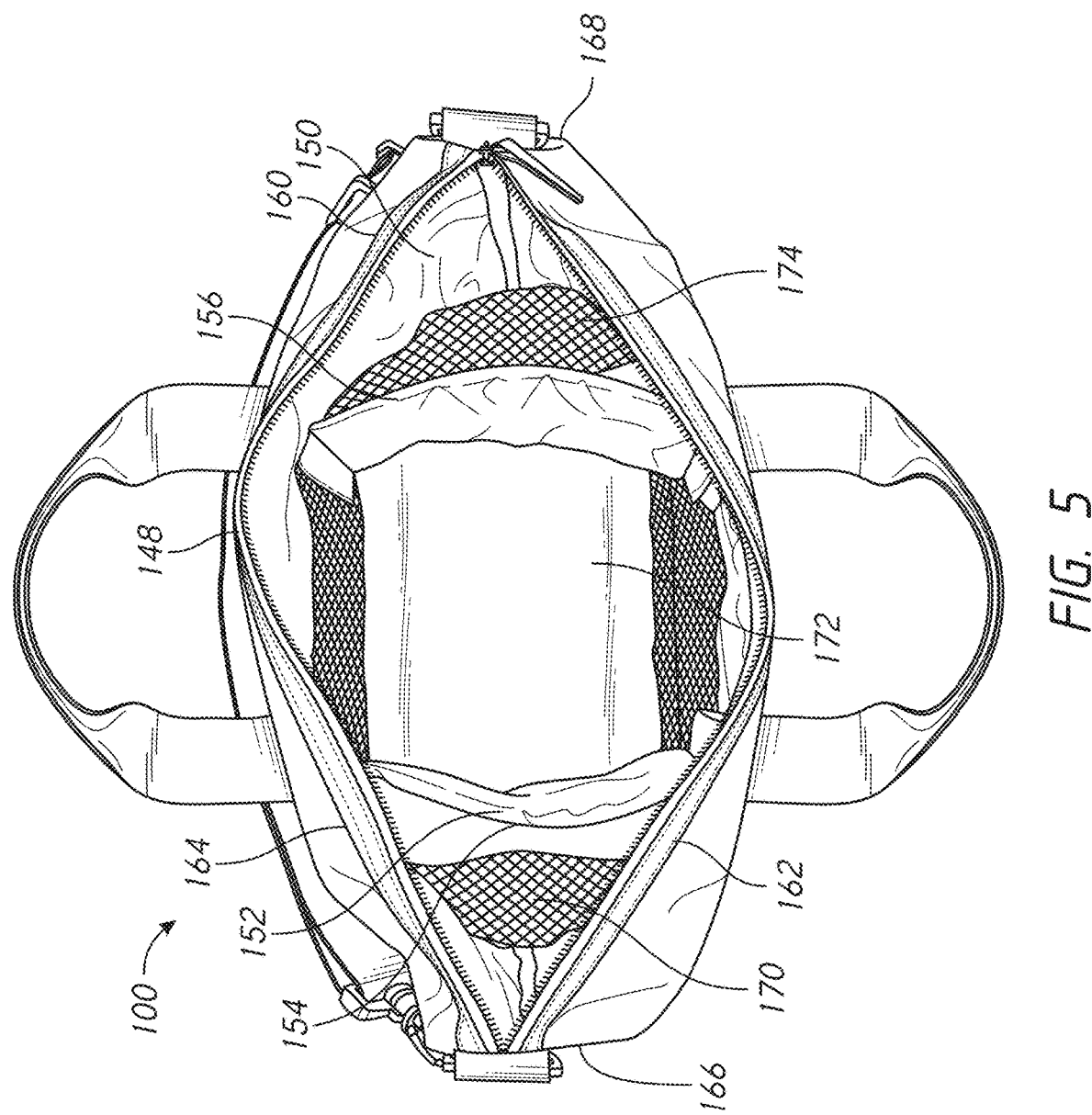
FIG. 5 shows a top view of an embodiment of the water dispersing bag including an interior.

FIG. 5 illustrates a top view of the bag 100, including an opening 148 surrounding an interior 150 of the bag 100. In some embodiments, the interior 150 can include one or more dividers 152. The one or more dividers 152 can include a first divider 154 and a second divider 156, for example. The dividers 152 can extend in several configurations between one or more side walls 160. For example, in the illustrated embodiment, the dividers 152 extend between a first side wall 162 and a second side wall 164. In some embodiments, the dividers 152 can extend between a third side wall 166 and a fourth side wall 168.

The dividers 152 can divide the interior 150 into a plurality of compartments. As shown in the illustrated embodiment, the dividers 152 can create a first side compartment 170, a central compartment 172 and a second side compartment 174. In some embodiments, the central compartment 172 can be configured to receive medical equipment and components, including electrical components.

Figure 6:
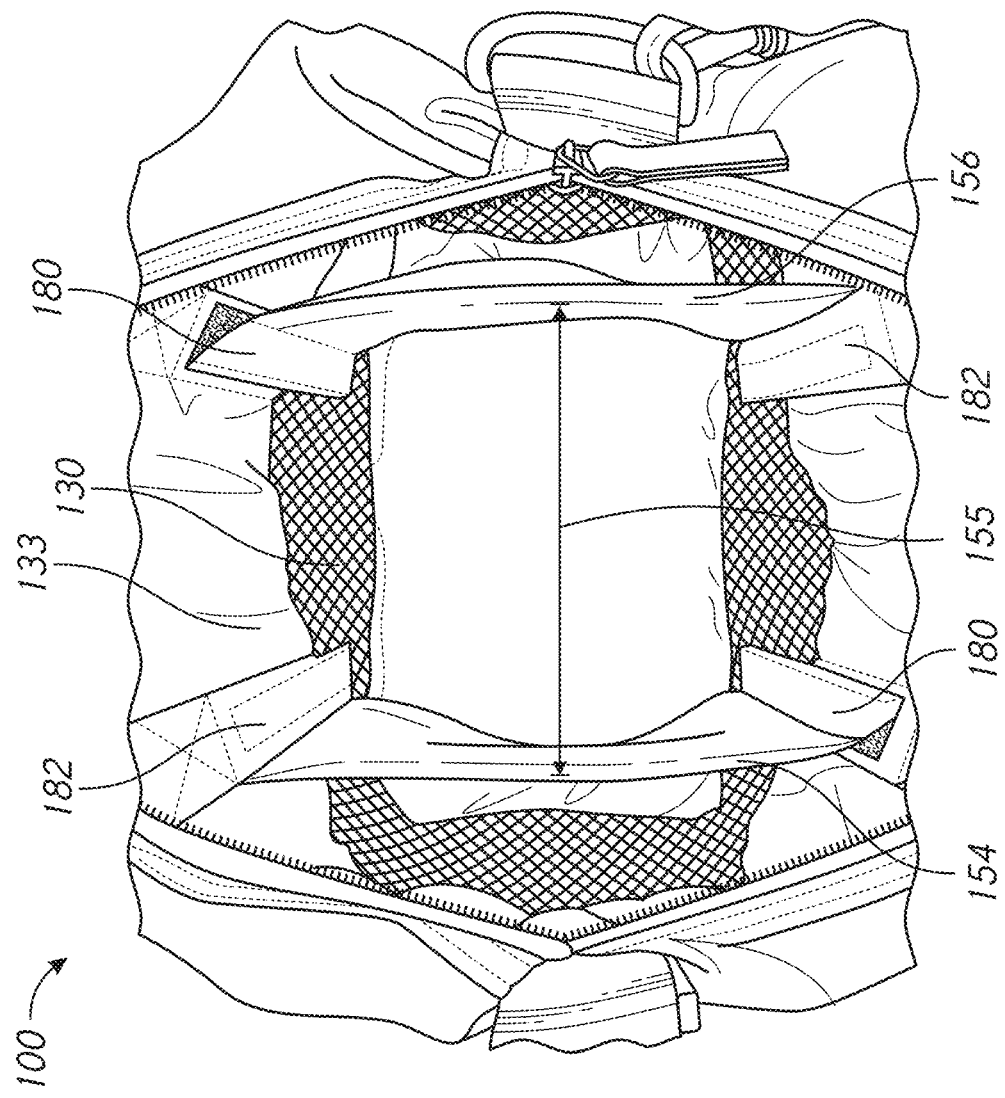
FIG. 6 shows a top view of an embodiment of the water dispersing bag including an interior.

FIG. 6 illustrates another example of the interior 150 of the bag 100. In some embodiments, the first and second dividers 154, 156 can be spaced apart a distance 155 of 180 mm. In some embodiments, the first and second dividers 154, 156 are spaced apart a distance 155 of greater than 180 mm. In yet other embodiments, the first and second dividers 154, 156 are spaced apart a distance 155 of less than 180 mm. Accordingly, in some embodiments, the first and second dividers 154, 156 can be longitudinally displaced approximately 90 mm from a longitudinal axis of the bag 100.

Each of the dividers 152 can be connected to the side walls 160 by a connection mechanism 180. In some embodiments a first end of the dividers 152 is fixed to a side wall of the side walls 160 and a second end of the dividers 152 can be connected by the connection mechanism 180. In some embodiments, the first end and the second end of the dividers 152 is fixed to a side wall of the side walls 160 to form a fixed connection 182. The connection mechanism can allow the dividers 152 to be connected or disconnected. For example, the connection mechanism can be a velcro connection that allows the dividers 152 to be connected and disconnected.

In some embodiments, the first divider 154 is fixed to the first side wall 162 and connected to the second side wall 164 by the connection mechanism 180. In such configurations, the second divider 156 can be connected to the first side wall 162 by the connection mechanism 180 and fixed to the second side wall 164. In some embodiments, the second divider is connected to the first and second side walls 162, 164 in the same way as the first divider 154. Yet, in other embodiments, the second divider 156 is connected to the first and second side walls 162, 164 in a different manner compared to the first divider 154.

Figure 7:
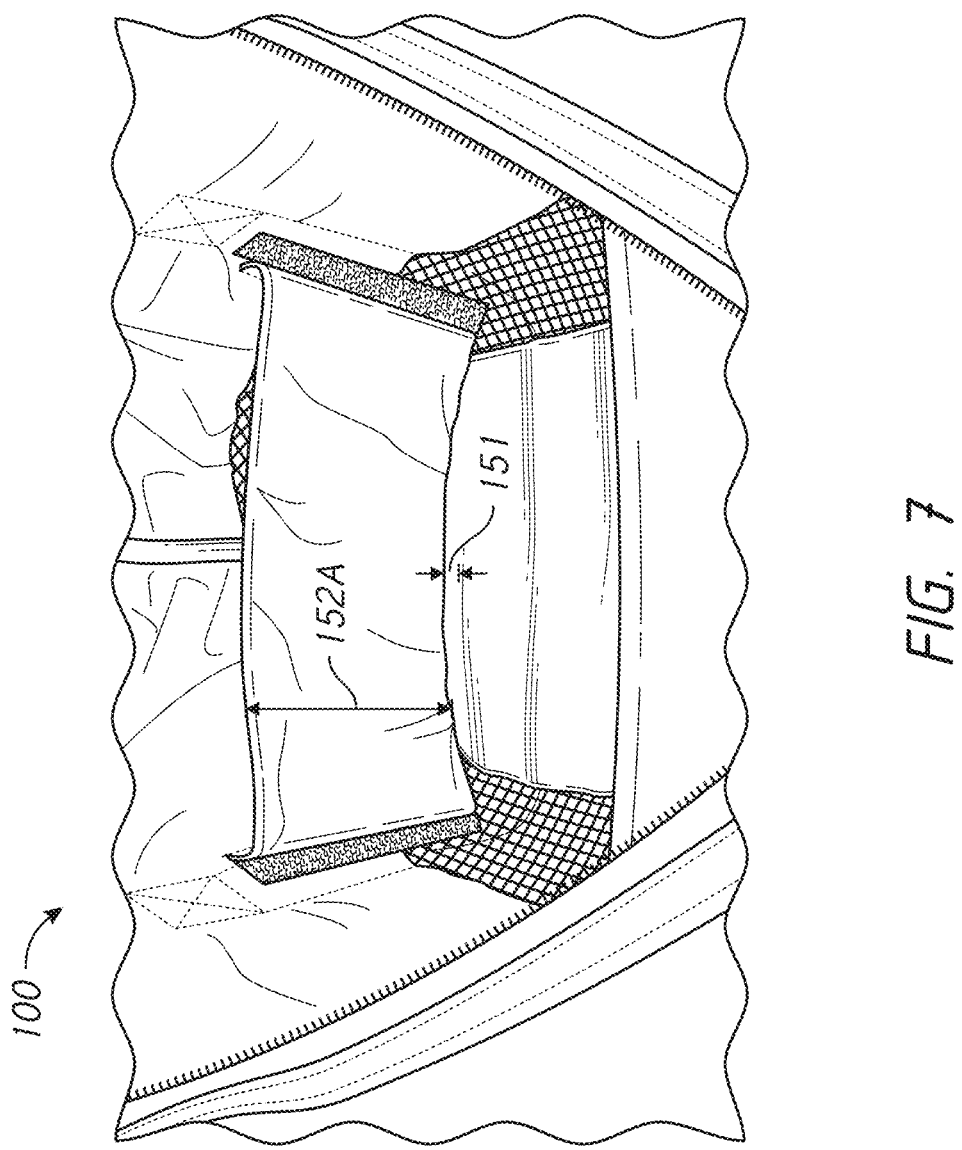
FIG. 7 shows a top view of an embodiment of the water dispersing bag including an interior.

FIG. 7 illustrates another view of the interior 150 of an embodiment of the bag 100. Each of the dividers 152 can have a height 152A of approximately 120 mm. In some embodiments, the height of the dividers 152 is more than approximately 120 mm. In some embodiments, the height of the dividers is less than 120 mm.

The bottom surface of each of the dividers 152 can be vertically displaced from an interior bottom surface of the interior 150. For example, the dividers 152 can be spaced vertically from the interior bottom surface by a height 151 of approximately 10 mm. In some embodiments, the dividers 152 can be spaced more or less than 10 mm from the interior bottom surface. Suspending the internal dividers above the bottom surface can allow liquid spilled or otherwise disposed within the interior 150 of the bag 100 to spread and/or disperse across compartments. For example, a liquid spilled in the first side compartment 170 would be able to spread across the central compartment 172 and the second side compartment 174. This could advantageously minimize the amount of time it takes for the liquid to drain from the bag through the lower portion 104, as the liquid can exit through each of the compartments.

In some embodiments, the dividers 152 can be made of one or more materials. For example, the dividers 152 can include a fabric such as polyester. In some embodiments, an insert can be disposed within the dividers 152. The insert of the dividers can include polyethylene foam, plastic, and/or silicone, among other materials. The material of the insert can be made of any material that is relatively rigid and/or deformable. In some embodiments, the insert does not span the entire length of the divider. In some embodiments, the dividers 152 can include one or more inserts of the same and/or different materials. In the illustrated embodiment, the insert spans the length of the divider. The connection mechanisms may not include an insert in some configurations. In some embodiments, the connection mechanisms can include the same, different, smaller, and/or larger inserts.

Figure 8A:
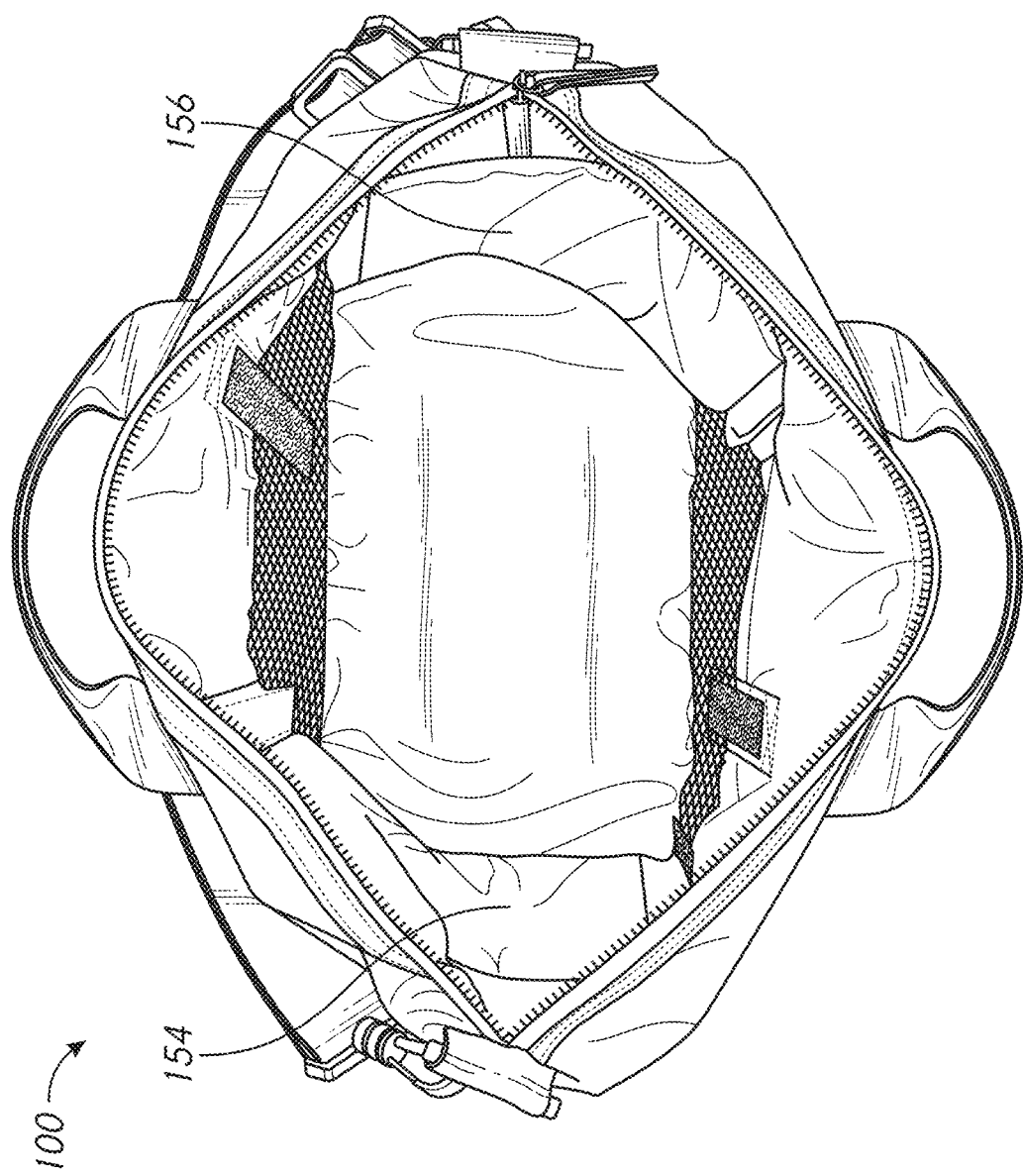
FIGS. 8A and 8B shows a top view of an embodiment of the water dispersing bag including an interior.
Figure 8B:
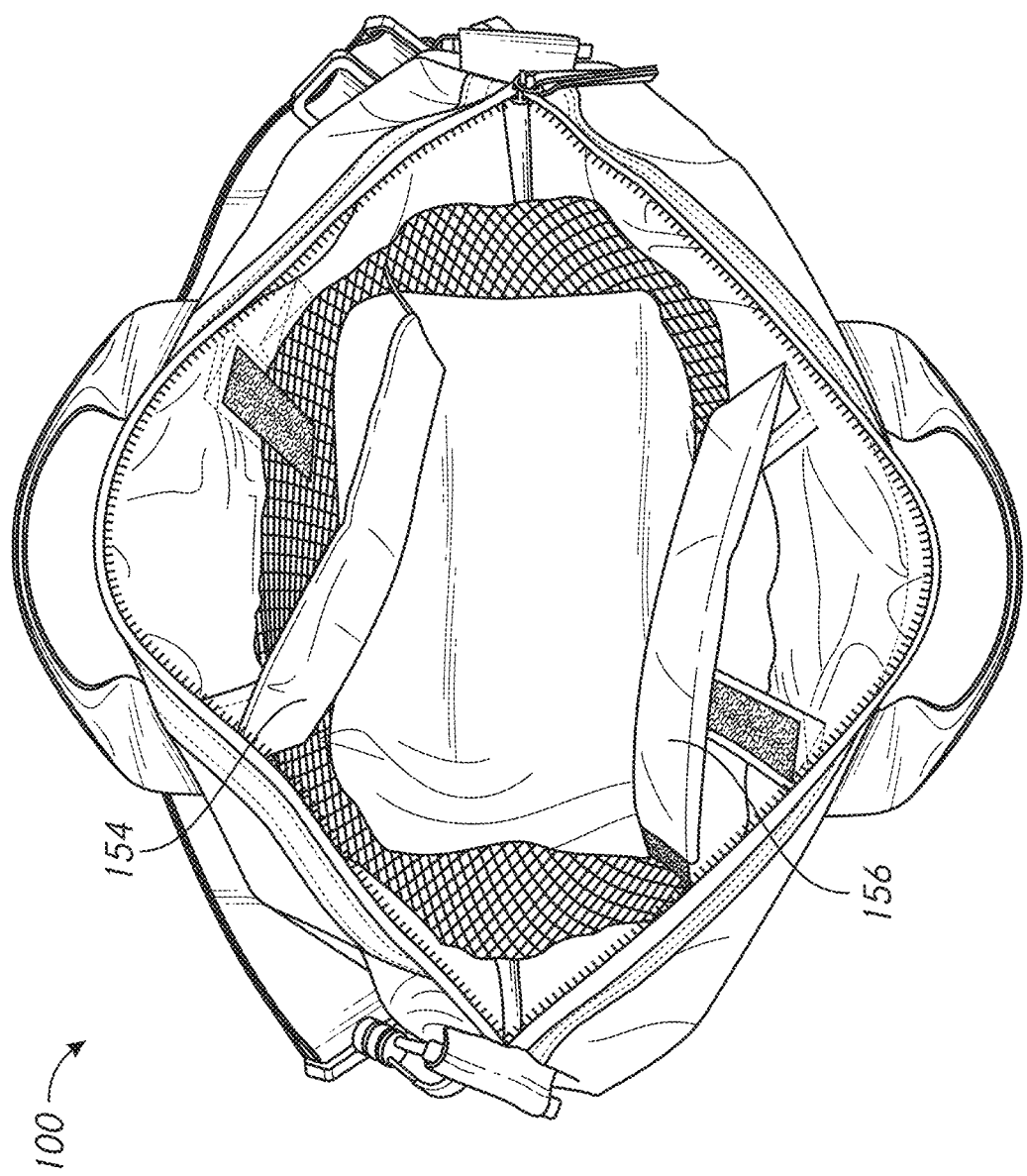

The dividers each can include the connection mechanism, such as a Velcro connection (See FIG. 6). In some configurations, as shown in FIGS. 8A and 8B, the connection mechanism 180 can be disconnected. In such configurations, the interior 150 of the bag 100 can include a single compartment. This configuration, as well as other configurations described herein, can allow the bag 100 to be used as a multipurpose bag, such that it can be used for transportation, storage, and/or other everyday uses.

FIG. 8A shows one configuration in which one compartment is formed within the interior 150 of the bag 100. In the illustrated configuration, each of the first and second dividers 154, 156 are disconnected from the connection mechanisms 180 and pivoted about the fixed connections 182 towards the third and fourth side walls 166, 168. FIG. 8B shows another configuration in which one compartment is formed within the interior 150 of the bag 100. In the illustrated configuration, each of the first and second dividers 154, 156 are disconnected from the connection mechanisms 180 and pivoted about the fixed connections 182 towards the first and second side walls 162, 164. Configurations including a single compartment can advantageously allow the bag 100 to be used as a multipurpose bag with a relatively large single compartment. This can allow the user to store, and/or transport more equipment, such as medical equipment, electronic equipment, and/or other materials within the bag 100. In some configurations, the first divider 154 can be disconnected from the connection mechanism 180 and can be pivoted about the fixed connection towards an adjacent side wall of the side walls 160. In such configurations, the second divider 156 can remain in place. In some configurations, the second divider 156 can be disconnected from the connection mechanism 180 and can be pivoted about the fixed connection towards an adjacent side wall of the side walls 160. In such configurations, the first divider 154 can remain in place. Accordingly, the interior of the bag can include two compartments.

In some embodiments, after the each of the first and second dividers 154, 156 are disconnected from the connection mechanisms and pivoted about respective fixed connections 182, the free end of each of the first and second dividers 154, 156 can connect to side connection mechanisms to hold the first and second dividers 154, 156 in place. Accordingly, a single compartment can be formed. For example, in the illustrated embodiment, a hook component of the connection mechanism 180, such as velcro, can be disposed on an end of the first and second dividers 154, 156. In such configurations, the hook component can attach to the first and/or second side walls 162, 164. In some embodiments, the hook component can attach to the side connection mechanisms of the first and second side walls 162, 164. In some embodiments, rather than the hook component, other attachment mechanisms can be used such as a button, latch, and/or the like. In such configurations, the first and second dividers 154, 156 can be retained by the side connection mechanisms to hold the dividers in place.

In some embodiments, the side connection mechanisms can be the same as the connection mechanism 180. For example, the first divider 154 can disconnect from the associated connection mechanism, pivot about the fixed connection, and connect to the connection mechanism of the second divider 156. In some embodiments, the second divider 156 can disconnect from the associated connection mechanism, pivot about the fixed connection, and connect to the connection mechanism of the first divider 154.

In some embodiments, as disclosed herein, implementing separate dividers 152 can have several advantages. For example, including separate dividers 152 in the bag 100 including at least one fixed connection can result in several manufacturing and/or logistical benefits. In some embodiments, the separate dividers 152 can reduce the risk that an operator will assemble the bag 100 incorrectly during manufacturing. Thus, the separate dividers 152 with at least one fixed connection can reduce the risk that the dividers 152 will be disposed in an incorrect position, such as upside down and/or fixed in the incorrect position.

In some embodiments, separate dividers 152 can allow the bag 100 to be folded and/or compressed efficiently. For example, FIG. 9 illustrates the bag in a compressed position. The compressed position can reduce the cost of shipping due to the smaller size during transport. The compressed position can reduce the overall size of the bag 100 such that it can be easily and/or efficiently stored, such as when the bag 100 is not in use.

Figure 10:
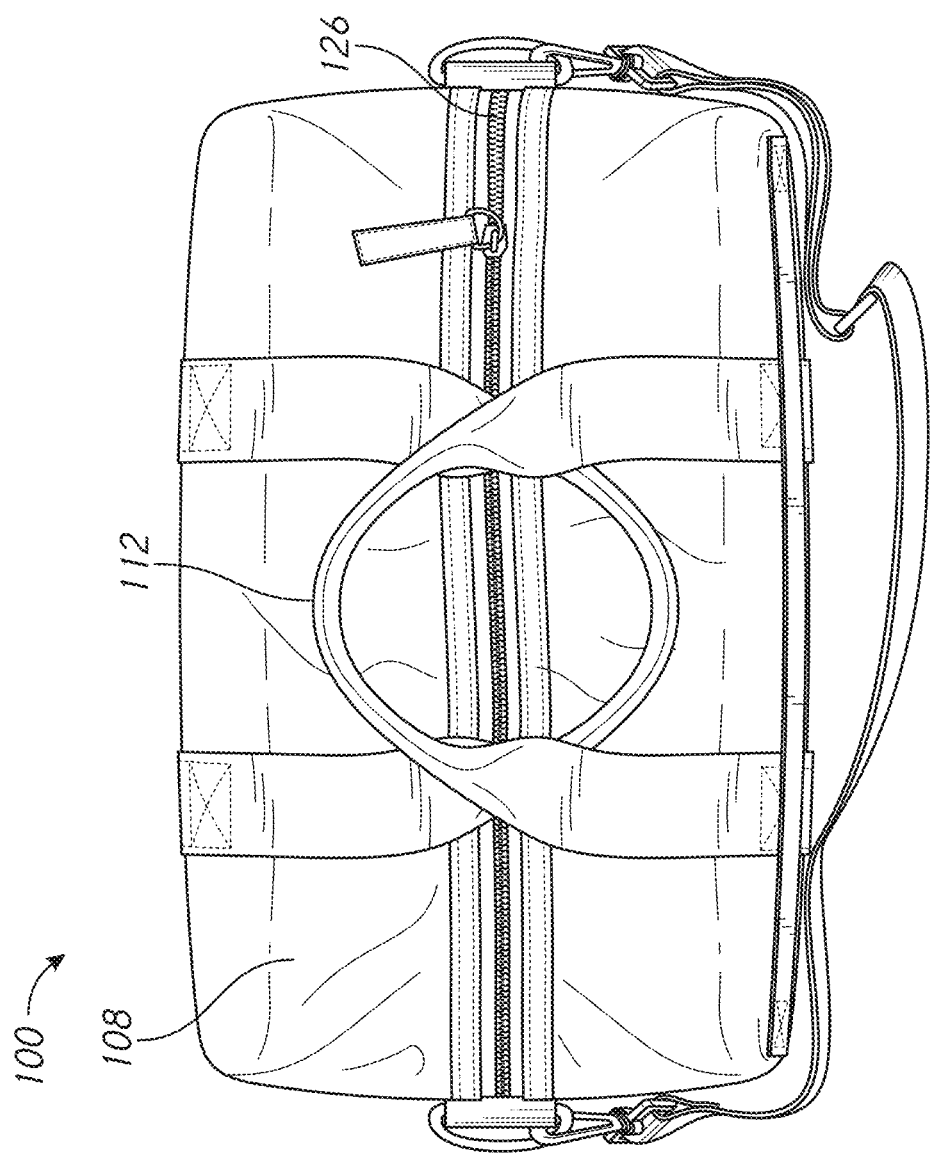
FIG. 10 shows a closed exterior top view of an embodiment of the water dispersing bag.

FIG. 10 illustrates a top view of an embodiment of the bag 100 in which the locking mechanism 126 is towards the closed position. In some embodiments, the locking mechanism 126 can include a zipper, a clasp, and/or at least one button, among others.

Figure 11:
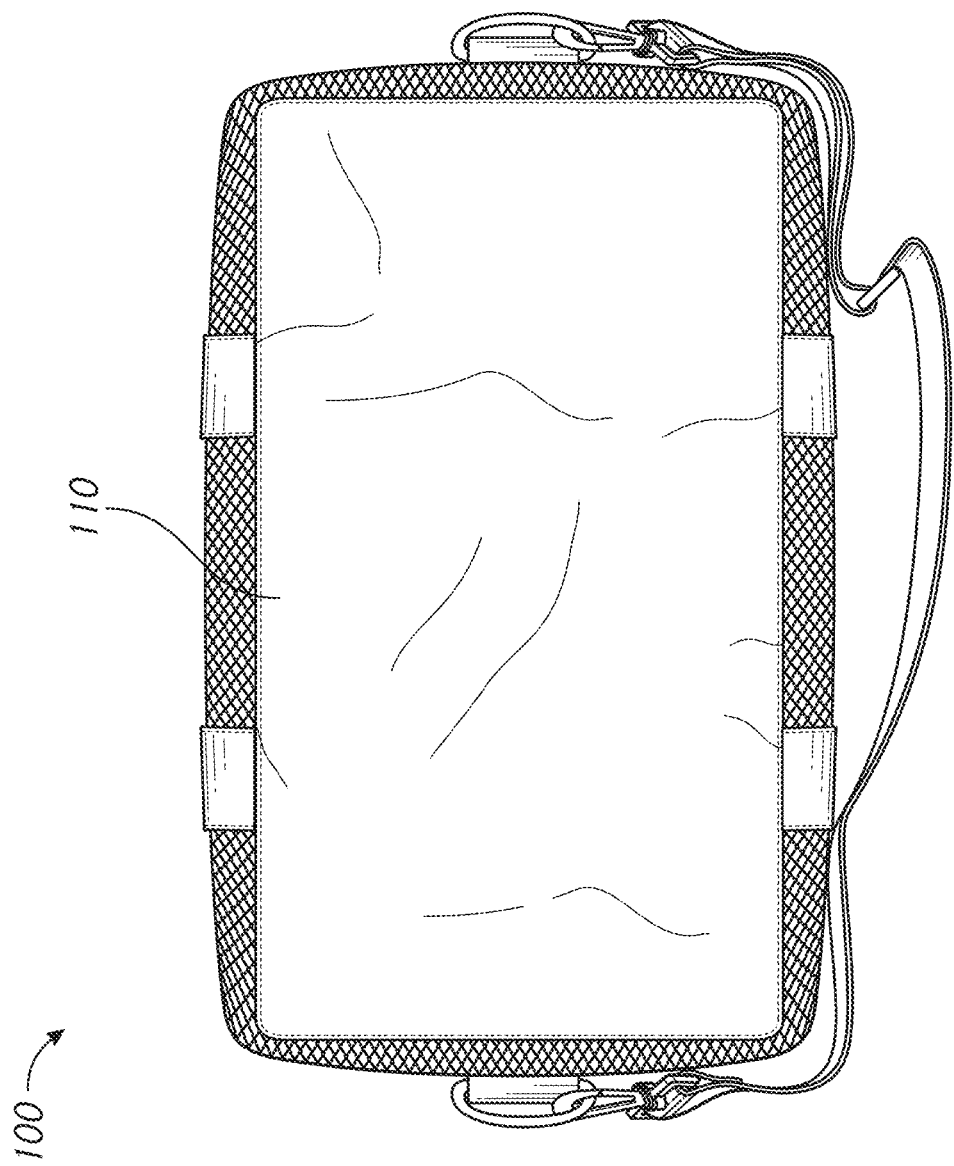
FIG. 11 shows an exterior bottom view of an embodiment of the water dispersing bag.

FIG. 11 illustrates a bottom view of an embodiment of the bag 100. As discussed above, the bag 100 can include a bottom surface 110. The bottom surface 110 can be made of one or more materials. For example, the bottom surface 110 can include fabric, such as polyester and/or black polyester canvas, among others. The bottom surface 110 can provide additional support for the bag 100. The bottom surface 110 can provide additional rigidity to the bag 100. Accordingly, the bottom surface 110 can allow the bag 100 to maintain the structural integrity.

In some embodiments, the bottom surface 110 can include an insert disposed between an exterior bottom surface and an interior bottom surface. In some configurations, the insert can include a foam-like material, such as black open cell 20 ppi or less filter foam. The insert can be 1 to 2, 2 to 3, 3 to 4, 4 to 5, 5 to 6, 6 to 7, 7 to 8, 8 to 9, and/or 9 to 10 or more mm thick. In some embodiments, the insert can include cells and/or gas pockets within the insert that can allow various amounts of liquid through the bottom surface and at various rates. As a result, the insert can provide channels for liquid to travel through and out of the bag with minimum resistance. Similarly, the bottom surface can be substantially permeable and/or allow liquid to pass through quickly. In some embodiments, the bottom surface 104 is less permeable than the lower portion 104 and the upper portion 108. In some embodiments, the insert of the bottom surface 110 can allow the bag to retain its shape in a plane of the bottom surface 110.

Handle

Figure 13:
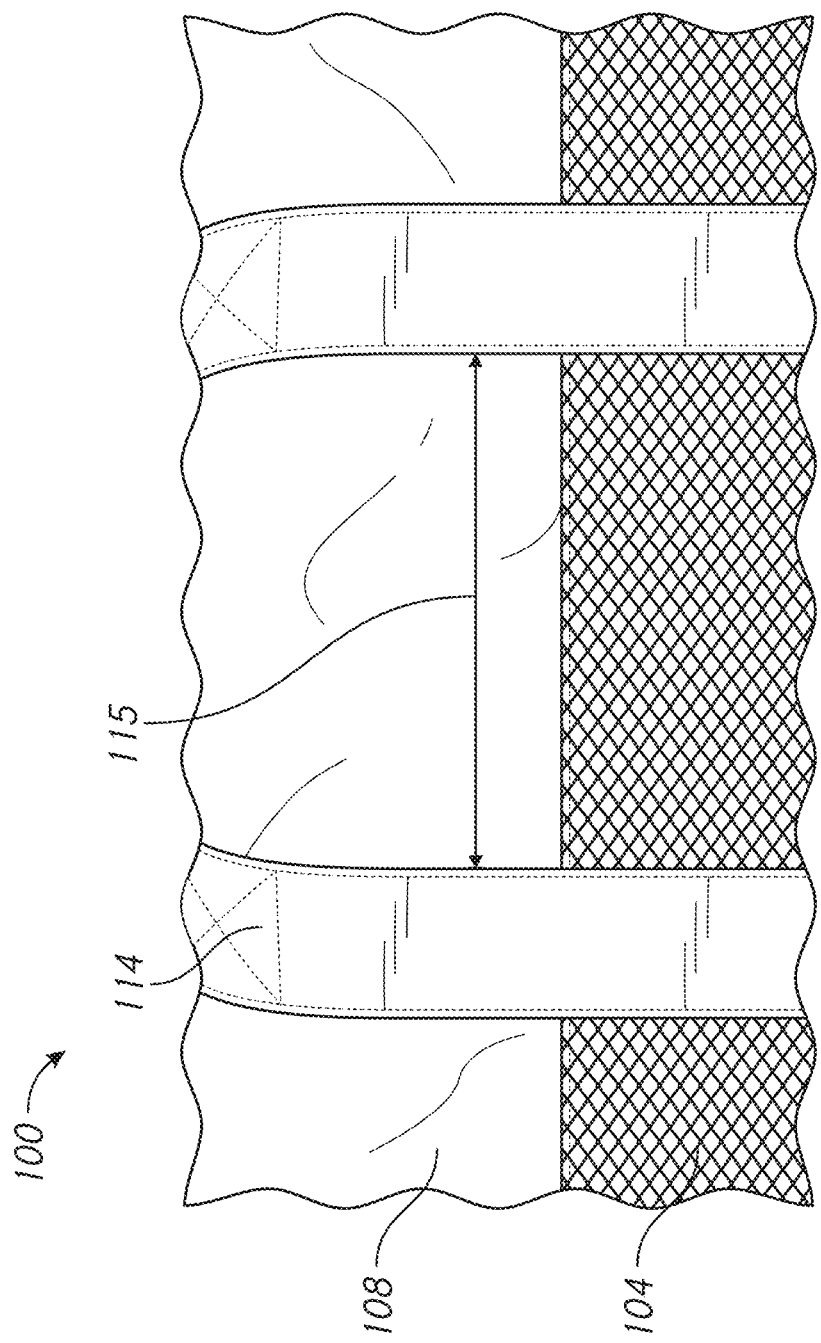
FIG. 13 shows a front of an embodiment of the water dispersing bag.

The bag 100 can include the handle 112. The handle 112 can include one or more handle straps 114. FIG. 13 illustrates an embodiment of the bag 100. In the illustrated configuration, the handle straps 114 can be spaced apart laterally by a handle strap spacing 115. In some embodiments, the handle strap spacing is approximately 110 mm. In some embodiments, the handle strap spacing 115 can be 50 to 100 mm, 100 to 125 mm, 125 to 150 mm, and/or 150 or more mm wide. The handle strap spacing 115 can vary along the length of the handle straps 114.

Figure 14A:
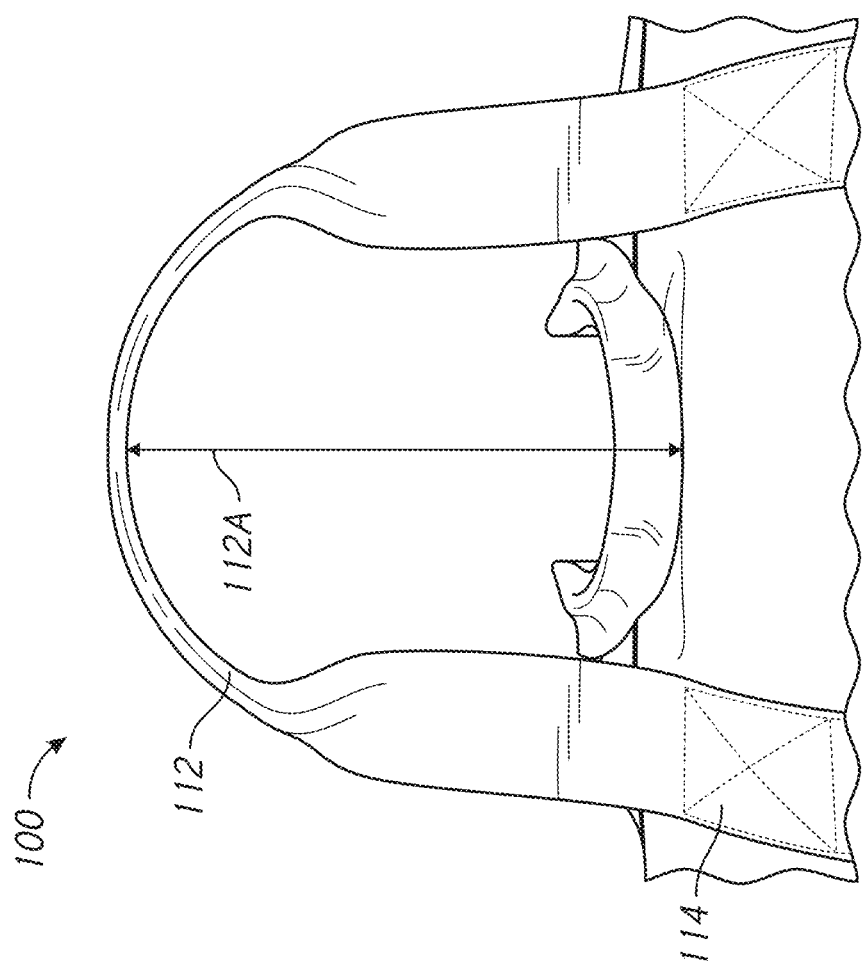

FIGS. 14A and 14B illustrate an embodiment of the handle 112. For example, in the illustrated embodiment, the handle 112 can extend upwardly from the upper portion 108. In some embodiments, the handle 112 can extend a handle height 112A from the upper portion 108. The handle height 112A can extend up to 150 mm, for example. In some embodiments, the handle height can extend a distance upwardly from the upper portion 108 greater than 150 mm. In some embodiments, the handle height 112A can extend a distance less than 150 mm from the upper portion 108.

In some embodiments, the handle 112 can have a handle width 112B, which can extend laterally in an interior portion of the handle 112. The handle width 112B can be advantageously sized to allow a user to comfortably and/or easily grip the handle 112. For example, the handle width 112B can be approximately 130 mm. In some embodiments, the handle width 112B is greater than 130 mm. In some embodiments, the handle width 112B is less than 130 mm.

Figure 15:
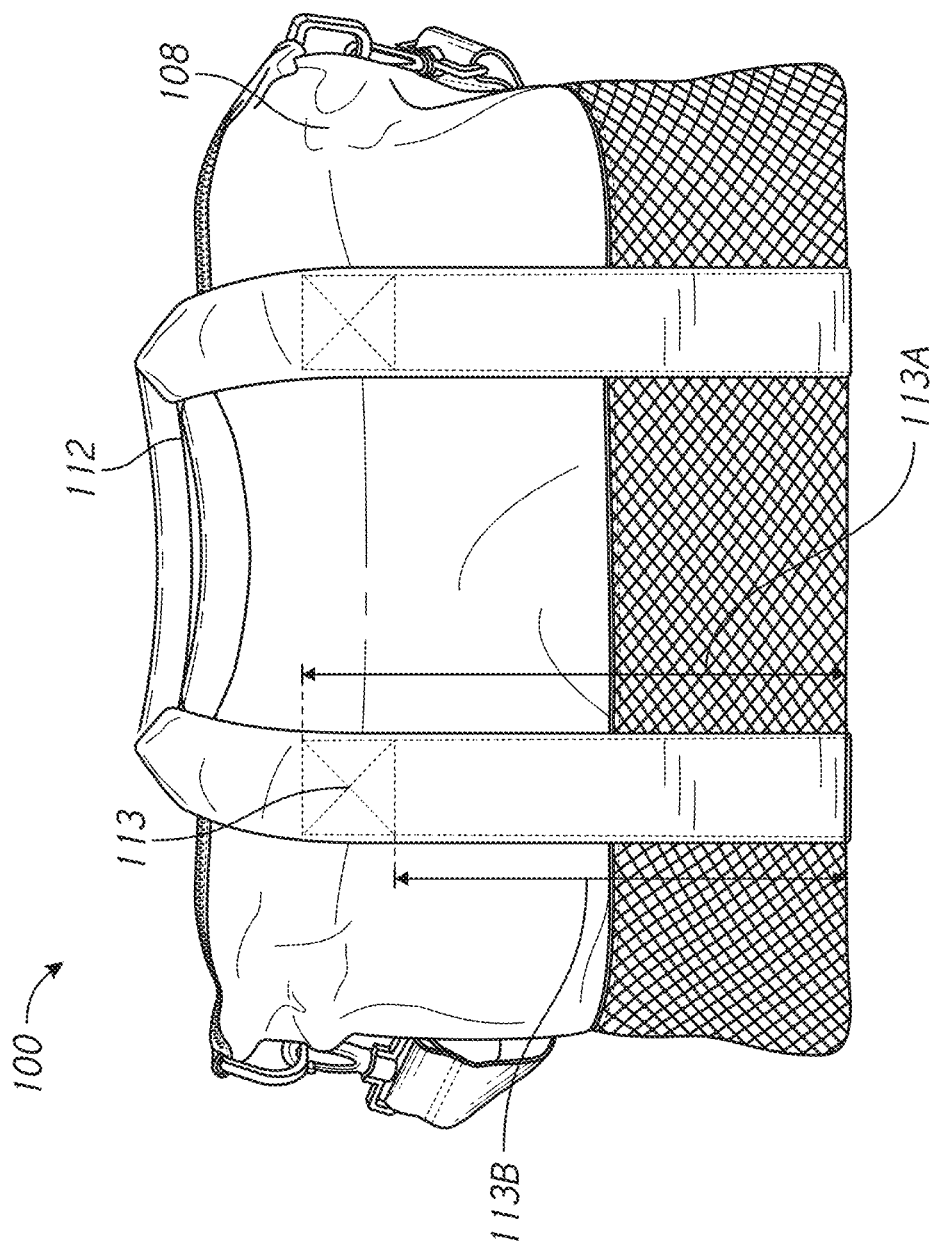
FIG. 15 shows a front view of an embodiment of the water dispersing bag.

In some configurations, the handle can be fixed to the bag 100 using various means. For example, FIG. 15 illustrates an example of the handle 112 and/or handle straps 114 connected to the bag 100. In the illustrated configuration, the handle 112 is fixed to the bag using a cross-stitching pattern 113. Other means can include other stitching patterns, adhesive, and/or the like. The cross-stitching pattern 113 can be fixed to the bag 100 through various means. For example, the pattern 113 can be stitched to the bag 100. The pattern 113 can be attached to the bag 100 by an adhesive. The cross-stitching pattern can allow for minimal attachment means to be used and can provide additional support to the handle 112. The cross-stitching pattern 113 can be sufficiently fixed to the upper portion 108 of the bag 100 such that it can withstand various weights and forces being applied to the handle 112 and/or bag 100.

In some embodiments, the cross-stitching pattern 113 can be attached to the upper portion 108 at various heights. In some configurations an upper end of the cross stitching pattern 113 is disposed at an upper cross stitching height 113A of approximately 180 mm. In some embodiments, the upper end can be disposed at a cross stitching height 113A greater than 180 mm. In some embodiments, the upper end can be disposed at a cross stitching height 113A less than 180 mm. In some configurations, a lower end of the cross stitching pattern 113 is disposed at a lower cross stitching height 113B of approximately 140 mm. In some embodiments, the lower end can be disposed at a cross stitching height 113B greater than 140 mm. In some embodiments, the lower end can be disposed at a cross stitching height 113B less than 140 mm.

Shoulder Strap

In some embodiments, the bag 100 can include the shoulder strap 120. The shoulder strap 120 can be detachable from the bag 100. In some embodiments, the shoulder strap is fixed to the bag 100.

Figure 12:
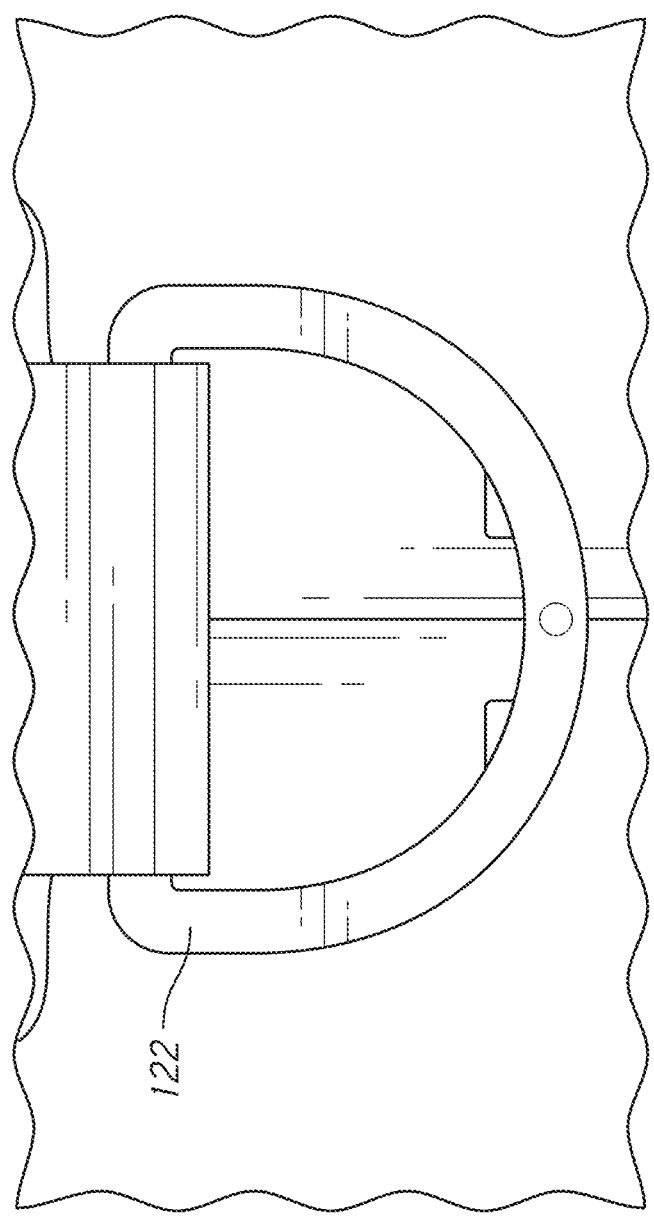
FIG. 12 shows an embodiment of a shoulder strap connector of the water dispersing bag.

The shoulder strap 120 can include at least one shoulder strap connector 122. The shoulder strap connector 122 can be fixed to the bag 100. In some embodiments, the shoulder strap connector can be detachable from the bag 100. In some embodiments, the shoulder strap connector 122 can be disposed at an upper end of the third and fourth side walls 166, 168. The shoulder strap connector 122 can allow for the shoulder strap 120 to be connected and/or disconnected from the bag 100. FIG. 12 illustrates an example of the shoulder strap connector 122. In the illustrated embodiment, the shoulder strap connector is in a D-ring shaped configurations. In some embodiments, the shoulder strap connector 122 can include an O-ring shape, among others. In some embodiments, the shoulder strap connector 122 can include plastic, metal, aluminum, and/or steel, among other materials.

Figure 16:
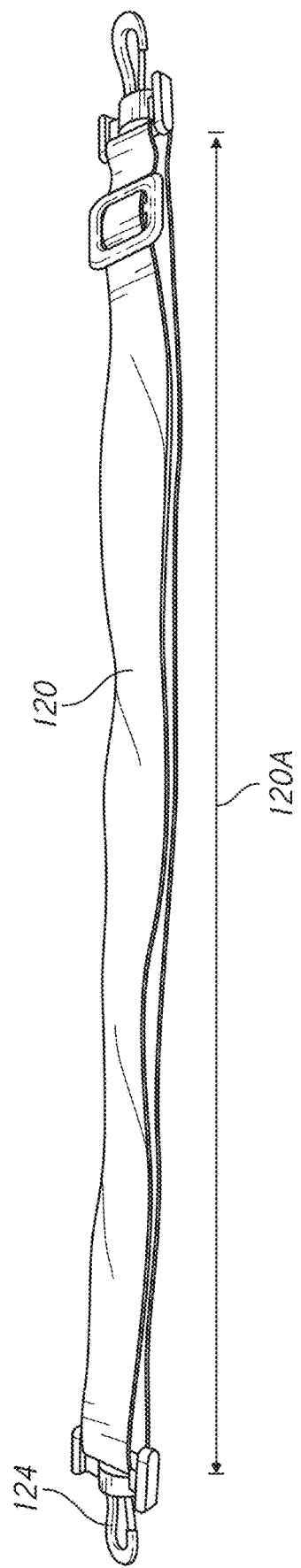
FIG. 16 shows an embodiment of a shoulder strap of the water dispersing bag.

FIG. 16 illustrates an embodiment of the shoulder strap 120. The shoulder strap can include a shoulder strap clip 124, among other attachment mechanisms. The shoulder strap clip 124 can be connected to the shoulder strap connector. In some embodiments, the shoulder strap clip 124 can connect directly to the bag 100.

In some embodiments, the shoulder strap 120 can be extendable. For example, in some configurations, the shoulder strap can have a minimum length and a maximum length. In such configurations, the minimum length 120A can be approximately 480 mm long. In some embodiments, the minimum length can be more or less than 480 mm long. In some embodiments, the maximum length can be approximately 500 to 600, 600 to 700, 700 to 800 and/or 800 or more millimeters long.

Figure 17:
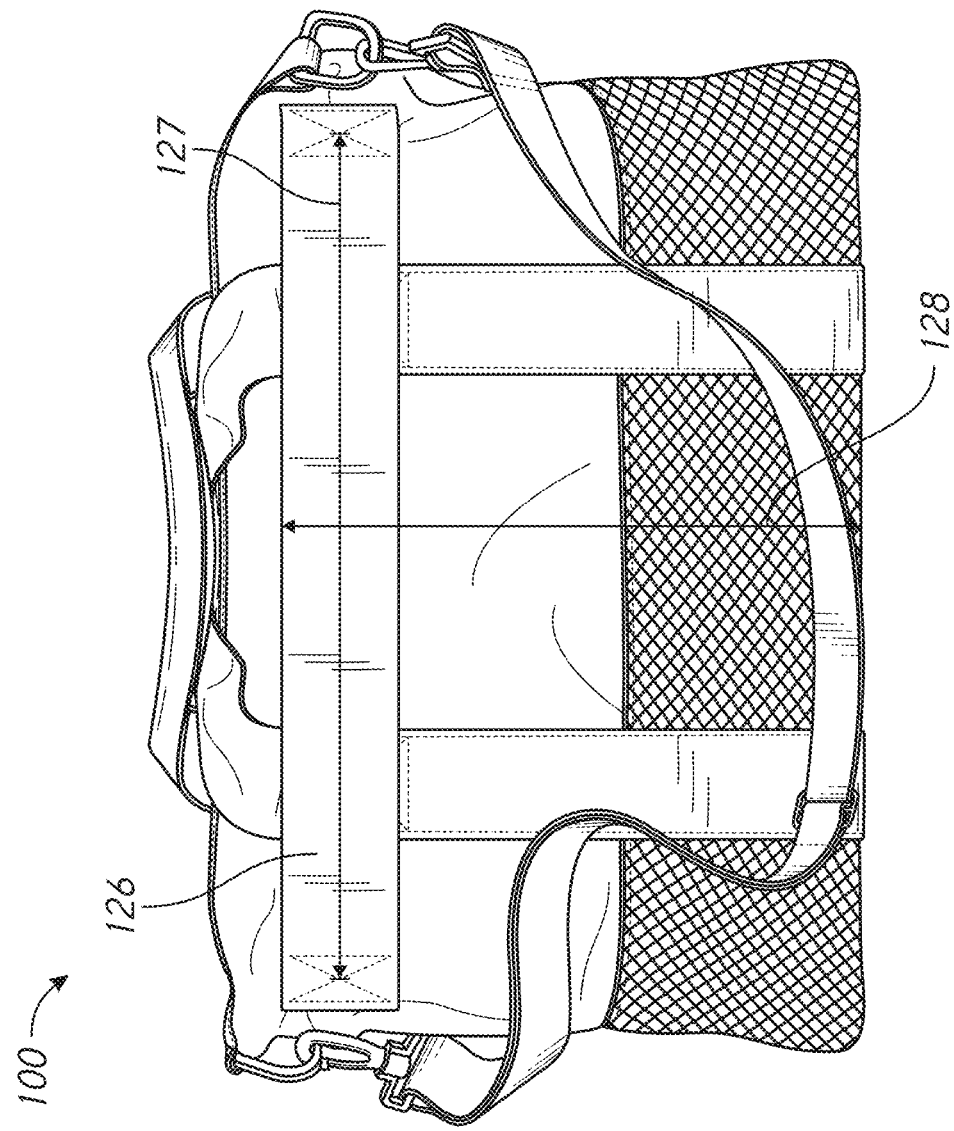
FIG. 17 shows a rear view of an embodiment of the water dispersing bag.

In some configurations, the bag 100 can include at least one luggage strap 126. The luggage strap 126 can be implemented in the bag 100 in addition to and/or in place of the shoulder strap 120. For example, FIG. 17 illustrates an embodiment of the bag 100 including a luggage strap 126. The luggage strap 126 can be fixed to the bag 100 in various locations. In some embodiments, the luggage strap 126 can be fixed to the bag 100 at any of the side walls. In the illustrated configuration, the luggage strap 126 is fixed to the bag 100 at the upper portion 108 of the second wall 164.

The luggage strap 126 can have a luggage strap length 127 that can span the longitudinal length of the bag 100. In some embodiments, the luggage strap length is equal to the width 109 of the upper portion 108. In some embodiments, the luggage strap length 127 can be less than the width 109 of the upper portion 108. For example, the luggage strap length 127 can be approximately 250 mm long. In some embodiments, the luggage strap length 127 can be greater than or less than 250 mm long.

In some embodiments, the luggage strap 126 can be disposed a luggage strap height 128 from the bottom surface of the bag 100. For example, a top edge of the luggage strap can be disposed at a luggage strap height 128 of approximately 180 mm. In some embodiments, the luggage strap height 128 can be greater than or less than 180 mm.

The luggage strap 126 can be attached to the bag 100 at various locations along the length of the luggage strap. For example, the luggage strap 126 can be attached to the bag 100 at one or more ends of the luggage strap. In some embodiments, the luggage strap 126 can be attached to the bag 100 at a central location. In some embodiments, the luggage strap 126 can be fixed to the bag 100. In some embodiments, the luggage strap 126 can be connectable and/or detachable from the bag 100.

Figure 18B:
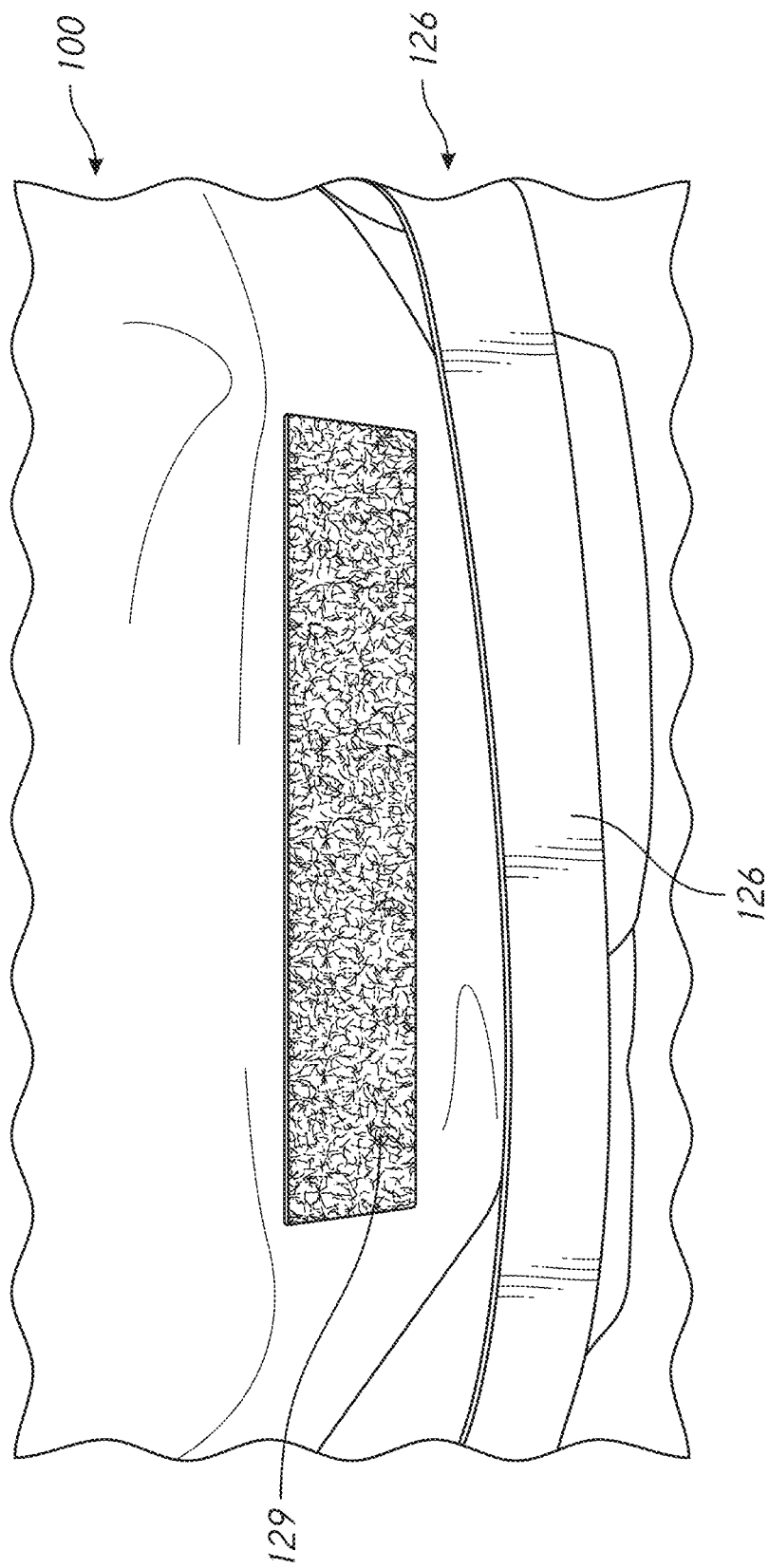

FIGS. 18A and 18B illustrate an embodiment of the luggage strap 126 that can be connectable and/or detachable from the bag 100 by a luggage strap connector 129. The luggage strap connector 129 can be centrally located with respect to the length of the luggage strap. In some embodiments, the luggage strap connector 129 can be offset from the center of the luggage strap 129. The luggage strap connector 129 can include any means of connection between the luggage strap 126 and the bag 100. For example, the luggage strap connector 129 can include a velcro connection, magnetic connection, push-fit mechanism, clasp, button, and/or snap mechanism, among others. The luggage strap connector can advantageously easily allow the user to attach and detach the luggage strap.

The luggage strap connector 129 can be fixed to the bag 100 by several means, such as stitching and/or an adhesive. The luggage strap connector can be sized and shaped to provide a secure connection and/or minimize space and/or material. For example, the luggage strap connector 129 can have a height 129A of approximately 20 mm. In some embodiments, the height 129A of the luggage strap connector 129 is greater than or less than approximately 20 mm. The luggage strap connector 129 can have a length 129B of approximately 60 mm. In some embodiments, the length 129B of the luggage strap connector 129 is greater than or less than approximately 60 mm.

The luggage strap connector 129 can securely hold the luggage strap 126 in place close to the bag 100. For example, FIG. 18B illustrates an embodiment of the luggage strap 126 and luggage strap connector 129. In the illustrated configuration, the luggage strap 126 is disconnected from the luggage strap connector 129. In such configurations, the luggage strap 126 can be displaced outwardly from the luggage strap connector 129 by approximately 25 mm. In some embodiments, the luggage strap 126 can be displaced outwardly from the luggage strap connector 129 at a maximum distance of greater than or less than approximately 25 mm.

CONCLUSION

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A water dispersing bag, the bag comprising:
   a bottom surface;
   a first side wall including:
      a lower portion with an insert,
      an upper portion, and
      wherein the lower portion is more permeable than the upper portion and the lower portion is configured to disperse and drain liquid out of the water dispersing bag;
   at least one divider,
      wherein the at least one divider divides an interior of the bag into a plurality of compartments, and
      wherein the at least one divider is spaced vertically away from the bottom surface;
   wherein the lower portion is positioned between the bottom surface and the upper portion; and
   wherein the bottom surface is less permeable than the lower portion.

2. The water dispersing bag of claim 1, wherein the lower portion extends at least partially around the bag.

3. The water dispersing bag of claim 1, wherein the insert of the lower portion comprises an open cell foam material and is disposed between a first layer of a mesh fabric and a second layer of a mesh fabric.

4. The water dispersing bag of claim 1, wherein the upper portion comprises a polyester canvas material.

5. The water dispersing bag of claim 1, wherein the bottom surface comprises a polyester canvas material.

6. The water dispersing bag of claim 1, further comprising a first handle strap spanning at least a first length of the first side wall, and a second handle strap spanning at least a second length of a second side wall.

7. The water dispersing bag of claim 1, further comprising an opening mechanism, the opening mechanism configured to allow access to an interior.

8. The water dispersing bag of claim 1, wherein a ratio between a vertical dimension of the lower portion to a vertical dimension of the first side wall is approximately 1:2.57.

9. The water dispersing bag of claim 1, wherein a vertical dimension of the lower portion is approximately 70 mm, and wherein a vertical dimension of the first side wall section is approximately 180 mm.

* * * * *